Figure 1A:
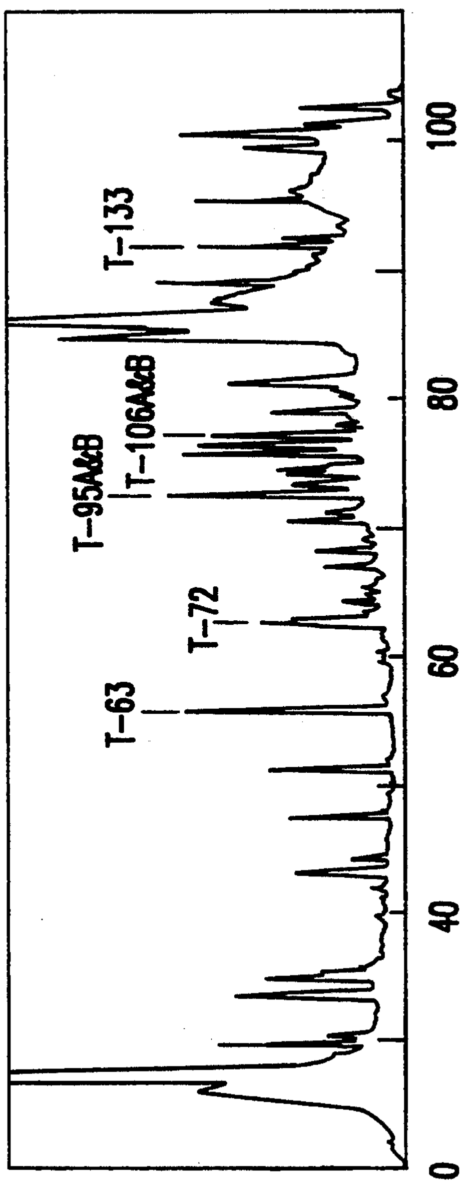

US005382524A

United States Patent [19]

Desnick et al.

[11] Patent Number: 5,382,524

[45] Date of Patent: Jan. 17, 1995

[54] CLONING AND EXPRESSION OF BIOLOGICALLY ACTIVE α-N-ACETYLGALACTOSAMINIDASE

[75] Inventors: Robert J. Desnick; David F. Bishop; Yiannis A. Ioannou; Anne M. Wang, all of New York, N.Y.

[73] Assignee: The Mount Sinai School of Medicine of the City University of New York, New York, N.Y.

[21] Appl. No.: 602,608

[22] Filed: Oct. 24, 1990

[51] Int. Cl.[6] .......................... C12N 15/00; C12N 9/40; C12N 9/24

[52] U.S. Cl. .......................... 435/200; 435/208; 435/172.1; 435/252.3

[58] Field of Search .................. 435/200, 172.1, 320.1, 435/208, 252.3; 935/14

[56] References Cited

PUBLICATIONS

Dean, K. J. et al., 1977, *Biochem. Biophys. Res. Commun.* 77(4): 1411–1417.
Schram, A. W. et al., 1977, *Biochimica et Biophysica Acta* 482: 138–144.
Sweeley, C. C. et al., 1983, *Archives of Biochemistry and Biophysics* 223(1): 158–65.
Tsuji, S. et al., 1989, *Biochem. Biophys. Res. Commun.* 163(3): 1498–1504.
Yamauchi, T. et al., 1990, *Biochem. Biophys. Res. Commun.* 170(1): 231–237.
Wang, A. M. et al., 1990, *J. Biol. Chem.* 265(35): 21859–21866.
Wang, A. M. et al., 1988, *Am. J. Hum. Genet.* 43(3 Suppl.): A99.
Schindler, D. et al., Jun. 29, 1989, *New Engl. J. Med.* 320(26): 1735–1740.
Desnick, R. J. et al., 1989, in The Metabolic Basis of Inherited Disease, Scriver, C. R., et al., eds. Ch. 70 entitled "Fabry Disease: α-Galactosidase Deficiency; Schindler Disease: α-N-Acetylgalactosaminidase Deficiency", pp. 1751–1796, McGraw Hill, New York.
Wang, A. M. et al., 1989, *Am. J. Hum. Genet.* 45(4 Suppl.): A228.
Wang, A. M. et al., 1990, *J. Clin. Invest.* 86: 1752–1756.
Desnick, R. J. and Wang, A. M., 1990, *J. Inher. Metab. Dis.* 13: 549–559.
Beutler, E. and Kuhl, W., 1972, *J. Biol. Chem.* 247(22): 7195–7200.
Callahan, J. W. et al., 1973, *Biochemical Medicine* 7: 424–431.
Kusiak, J. W. et al., 1978, *J. Biol Chem.* 253(1): 184–190.
Dean, K. J. and Sweeley, C. C., 1979, *J. Biol Chem.* 254(20): 10001–10005.
Bishop, D. F. et al., 1980, in Birth Defects: Original Article Series, XVI(1): 17–32 Desnick, R. J. et al., Editors Alan R. Liss, Inc., New York.

*Primary Examiner*—Robert A. Wax
*Assistant Examiner*—Keith D. Hendricks
*Attorney, Agent, or Firm*—Pennie & Edmonds

[57] ABSTRACT

The present invention involves the production of human α-GalNAc by cloning and expressing the α-GalNAc coding sequence in eukaryotic host cell expressions systems. The eukaryotic expression systems, and in particular the mammalian host cell expression systems described herein provide for the appropriate co-translational and post-translation modifications required or proper processing, e.g., glycosylation, phosphorylation, etc. and sorting of the expression product so that an active enzyme is produced.

The α-GalNAc produced in accordance with the invention may be used in the treatment of Schindler disease or for the hydrolysis of α-N-acetylgalactosaminyl moieties in various glycoconjugates.

20 Claims, 14 Drawing Sheets

```
-344                  CTTAAGCCAGTGGCTGCCTTTTTCTGAGCCCGGGCGGGGCCGAAGGC
-239 ACGTTGTTTCGTATTTCTGAAGGAAGAACTCAAGCTCCGGGAAGTGATGGCTGGGGATGG
-119 AGCCAGGCAGCCGTGACCCCAGTGCTTTTCAGACGTTTCTTAGCTTCCAGAGCCCAACAC

   1 ATG CTG CTG AAG ACA GTG CTC TTG CTG GGA CAT GTG GCC CAG GTG
   1 Met Leu Leu Lys Thr Val Leu Leu Leu Gly His Val Ala Gln Val

  91 CTG GCC TGG GAA CGC TTC CGC TGC AAC ATT AAC TGT GAT GAG GAC
  31 Leu Ala Trp Glu Arg Phe Arg Cys Asn Ile Asn Cys Asp Glu Asp
     ___________________________________________________________

 181 CGG ATG GCA CAG GAT GGA TGG CGG GAC ATG GGC TAC ACA TAC CTA
  61 Arg Met Ala Gln Asp Gly Trp Arg Asp Met Gly Tyr Thr Tyr Leu
                         T-106A ____________________________

 271 CTG ATG CCA GAT CCC AAG CGC TTC CCT CAT GGC ATT CCT TTC CTG
  91 Leu Met Pro Asp Pro Lys Arg Phe Pro His Gly Ile Pro Phe Leu

 361 GAC ATG GGC AAC TTC ACC TGC ATG GGT TAC CCA GGC ACC ACA CTG
 121 Asp Met Gly Asn Phe Thr Cys Met Gly Tyr Pro Gly Thr Thr Leu
            CHO ----------

 451 GAC ATG CTC AAG CTG GAT GGC TGC TTC TCC ACC CCC GAG GAG CGG
 151 Asp Met Leu Lys Leu Asp Gly Cys Phe Ser Thr Pro Glu Glu Arg

 541 CGC CCC ATC GCC TTC TCC TGC AGC TGG CCA GCC TAT GAA GGC GGC
 181 Arg Pro Ile Ala Phe Ser Cys Ser Trp Pro Ala Tyr Glu Gly Gly
  T-95B _____________________________________________________
```

CONT. ON FIG. 2B

FIG. 2A

CONT. FROM FIG.2A

GCCCGTAGGCCCTCGGGACTCCCAGCACTGCAGAGGGTGTGAGGTCTGACATCCAAGAC -240
GGCGGGCAACTTGGGGACCGAGTGTACGATCCACGCCTAAGGTTGAGGGCGGCCGAGCT -120
ATACAGCTGATACACGCAGACCAGATCTGGTCAGGTCCTCGGAAGCTGAGTCCAGAGCG - 1

CTG ATG CTG GAC AAT GGG CTC CTG CAG ACA CCA CCC ATG GGC TGG 90
Leu Met Leu Asp Asn Gly Leu Leu Gln Thr Pro Pro Met Gly Trp 30
N-Ter

CCA AAG AAC TGC ATA AGT GAA CAG CTC TTC ATG GAG ATG GCT GAC 180
Pro Lys Asn Cys Ile Ser Glu Gln Leu Phe Met Glu Met Ala Asp 60
T-106B

AAC ATT GAT GAC TGC TGG ATC GGC GGT CGC GAT GCC AGT GGC CGC 270
Asn Ile Asp Asp Cys Trp Ile Gly Gly Arg Asp Ala Ser Gly Arg 90

GCT GAC TAC GTT CAC TCC CTG GGC CTG AAG TTG GGT ATC TAC GCG 360
Ala Asp Tyr Val His Ser Leu Gly Leu Lys Leu Gly Ile Tyr Ala 120

GAC AAG GTG GTC CAG GAT GCT CAG ACC TTC GCC GAG TGG AAG GTA 450
Asp Lys Val Val Gln Asp Ala Gln Thr Phe Ala Glu Trp Lys Val 150
T-72

GCC CAG GGG TAC CCC AAG ATG GCT GCT GCC CTG AAT GCC ACA GGC 540
Ala Gln Gly Tyr Pro Lys Met Ala Ala Ala Leu Asn Ala Thr Gly 180
CHO

CTC CCC CCA AGG GTG AAC TAC AGT CTG CTG GCG GAC ATC TGC AAC 630
Leu Pro Pro Arg Val Asn Tyr Ser Leu Leu Ala Asp Ile Cys Asn 210
CHO

FIG.2B

```
 631  CTC TGG CGT AAC TAT GAT GAC ATC CAG GAC TCC TGG TGG AGC GTG
 211  Leu Trp Arg Asn Tyr Asp Asp Ile Gln Asp Ser Trp Trp Ser Val

 721  CCA GTG GCC GGC CCT GGG CAC TGG AAT GAC CCT GAC ATG CTG CTC
 241  Pro Val Ala Gly Pro Gly His Trp Asn Asp Pro Asp Met Leu Leu

 811  GCC CTG TGG ACG GTG CTG GCA GCC CCC CTC TTG ATG TCC ACA GAC
 271  Ala Leu Trp Thr Val Leu Ala Ala Pro Leu Leu Met Ser Thr Asp
      ___________________________________________________________

 901  CTC ATG ATC AAA ATC AAC CAG GAT CCC TTA GGC ATC CAG GGA CGC
 301  Leu Met Ile Lys Ile Asn Gln Asp Pro Leu Gly Ile Gln Gly Arg
                  T-63 _____________________________________________

 991  CTG TCC AAC AAG GCT AGC GCC TTA GTC TTC TTC AGC TGC AGG ACC
 331  Leu Ser Asn Lys Ala Ser Ala Leu Val Phe Phe Ser Cys Arg Thr
                 T-95A _________________________________________

1081  ACC GGG TCT GTG ATA TAT GAG GCC CAG GAC GTC TAC TCA GGT GAC
 361  Thr Gly Ser Val Ile Tyr Glu Ala Gln Asp Val Tyr Ser Gly Asp
      ---

1171  AAC CCT TCA GGG GTA GTG ATG TGG TAC CTG TAT CCC ATC AAG AAC
 391  Asn Pro Ser Gly Val Val Met Trp Tyr Leu Tyr Pro Ile Lys Asn
  CHO ----------

1268  ACCACTGAGCCTAGACCATGGAGCCTTGGCATGCCCAGGGCAAGTGGGGAGGTTCTCTGC
1387  TTCTATGCCCTGTCCAAGCGTAAACCCTCTTGGAAACTTCTTTTGGGGCAATTTTCCTGT
1506  CAGCCTCCTGAGCTCCATGCCCATCAGGACTCTAGCCTCTGACCTTGCTGTTGACTCTGA
1625  GCCCATGGATCATGTGATTGGCTTTTCTACCCATAGAGGGCCTTGCAGCCTGATACCACT
1744  TAATCAAAAAAAAAAAAAAAAAAAAAAAAAAAAAAAAAAAAAAAAAAAAAAAAAAAAAAA
```

CONT. ON FIG. 2D

FIG. 2C

CONT. FROM FIG.2C

```
CTC TCC ATC CTG AAT TGG TTC GTG GAG CAC CAG GAC ATA CTG CAG    720
Leu Ser Ile Leu Asn Trp Phe Val Glu His Gln Asp Ile Leu Gln    240

ATT GGG AAC TTT GGT CTC AGC TTA GAG CAA TCC CGG GCC CAG ATG    810
Ile Gly Asn Phe Gly Leu Ser Leu Glu Gln Ser Arg Ala Gln Met    270
                                            T-133 ----------

CTG CGT ACC ATC TCC GCC CAG AAC ATG GAC ATT CTG CAG AAT CCA    900
Leu Arg Thr Ile Ser Ala Gln Asn Met Asp Ile Leu Gln Asn Pro    300
-------

AGG ATT CAC AAG GAA AAA TCT CTC ATC GAA GTG TAC ATG CGG CCT    990
Arg Ile His Lys Glu Lys Ser Leu Ile Glu Val Tyr Met Arg Pro    330

GAT ATG CCT TAT CGC TAC CAC TCC TCC CTT GGC CAG CTG AAC TTC   1080
Asp Met Pro Tyr Arg Tyr His Ser Ser Leu Gly Gln Leu Asn Phe    360
                                                CHO -------

ATC ATC AGT GGC CTC CGA GAT GAA ACC AAC TTC ACA GTG ATC ATC   1170
Ile Ile Ser Gly Leu Arg Asp Glu Thr Asn Phe Thr Val Ile Ile    390
                                CHO -----------

CTG GAG ATG TCC CAG CAG TGA GGAGCTGGGACATGTGACAGGCTGTGGTGGC   1267
Leu Glu Met Ser Gln Gln End                                    411

TCCCCAGGCCTGCTCGGTGACTGACCCCATCATACCCAAAGTGCAATCTCACGGCCAGG   1386
GGCCTTCCTGGCCTCTACTTCCATGTGCGCAGCCCCACAGACGTTGCTGAGCAACTCGC   1505
AATCAGGATTTGGAAGTTTTCGAATTAGGAGTAGAGAGATCTGACCTCTTGCCAGGAAT   1624
GGGAGTGAGGGTCACAAAGGAGACCTTGGCTCCCTCAGGTCACCAATAAACCTGTTCTT   1743
AAAAAAAAAAA                                                   1814
```

FIG.2D

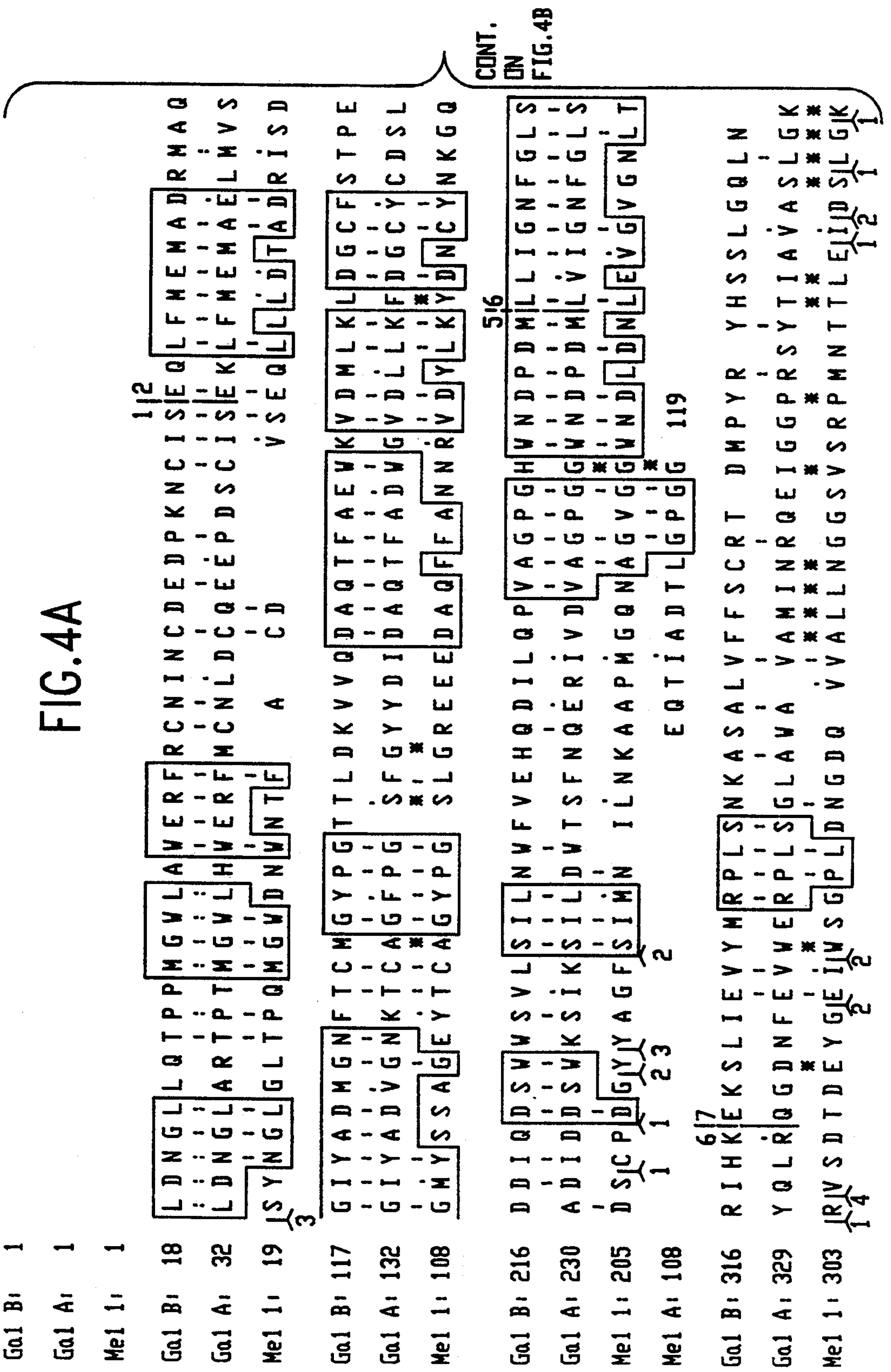

FIG.4A

Figure 4B:
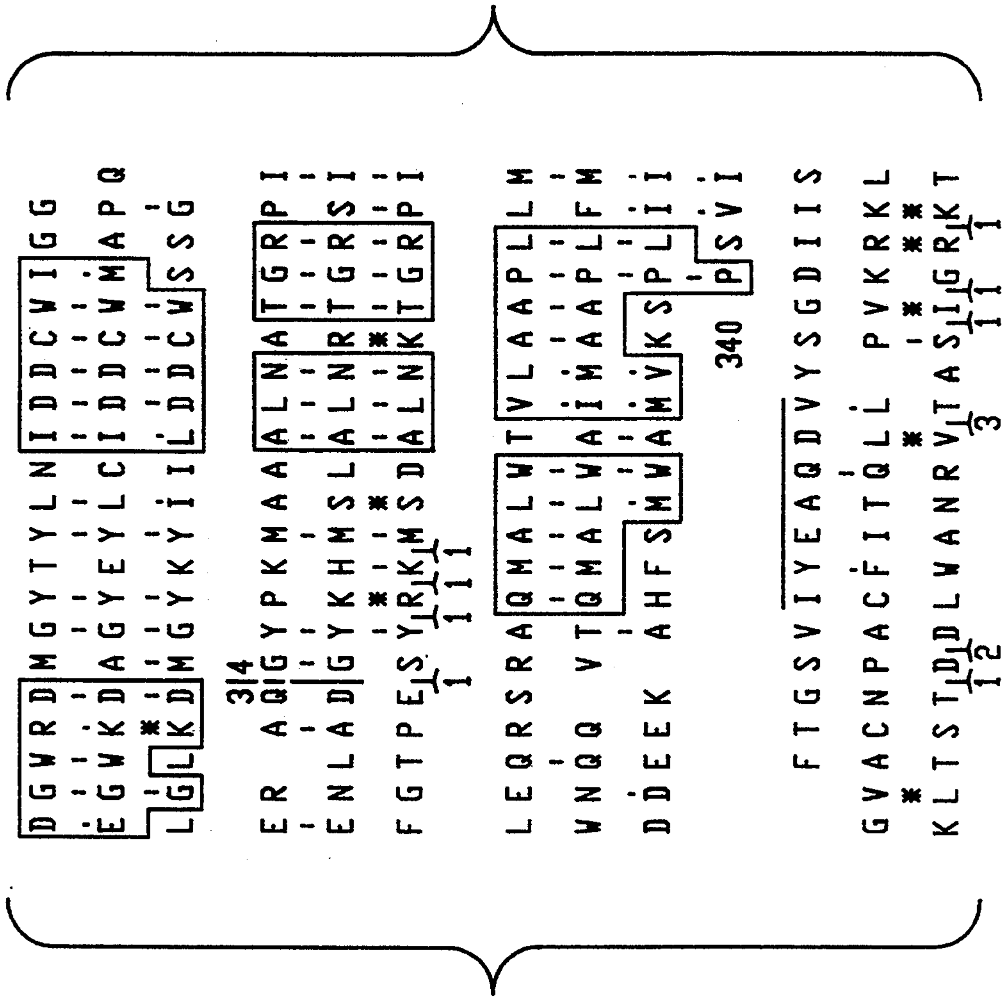

```
Gal B: 1                                                         LDNGLLQTPPMGVLAWERFRCNINCDEDPKNCISEQLFMEMADRMAQ
Gal A: 1                                                         LDNGLARTPTMGVLHWERFMCNLDCQEEPDSCISEKLFMEMAELMVS
Mel I: 1                                                         SYNGLGLTPQMGWDNWNTF      A   CD         VSEQLLDTADRISD
                                                                                                                    1|2
Gal B: 18    GIYADMGNFTCMGYPGTTLDKVVQDAQTFAEWKVDMLKLDGCFSTPE
Gal A: 32    GIYADV GNKTCAGFPG    - SFGYYDIDAQTFADWGVDLLKFDGCYCDSL
Mel I: 19    GMYSSAGEYTCAGYPG   *  SLGREEEDAQFFANNRVDYLKYDNCYNKGQ
              3
Gal B: 117   DDIQDSWSVLSILNWFVEHQDILQPVAGPGHVNDPDMLLIGNFGLS
Gal A: 132   ADIDDSWKSIKSILDVTSFNQERIVD - AGP - - GWNDPDMLVIGNFGLS
Mel I: 108   DSCPDGIY AGFSIMN ILNKAAPMGQNAGVGGWNDLDNLEVGVGNLT
                  1 1                                              5 6
                  2 3                                                                               CONT.
                  6|7                  EQTIADTLGPGG  119                                            ON
Gal B: 216   RIHKEKSLIEVYMRPLSNKASALVFFSCRT DMPYR YHSSLGQLN       FIG.4B
Gal A: 230   YQLRQGDNFEVWERPLSGLAVA  VAMINRQEIGGPRSYTIAVASLGK
Mel I: 303   RIVSDTDEYGE IWSGPLDNGDQ  VVALLNGGSVSRPMNTTLEID SLGK
              1 4                 2                                              1 2  1|1
```

CONT. ON FIG.4C

CONT. FROM FIG.4A

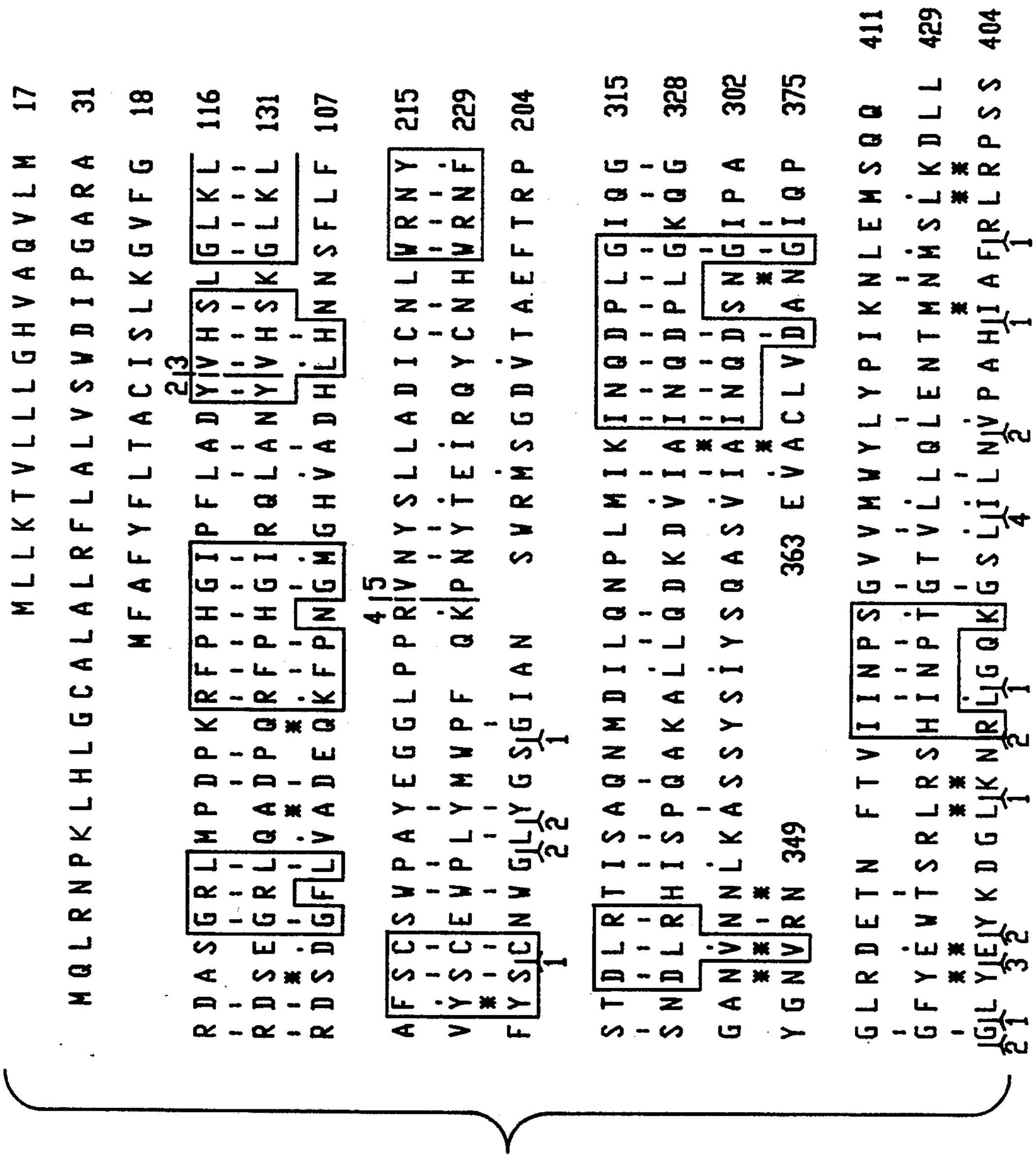

FIG.4C

CONT. FROM FIG.4B

```
                    M L L K T V L L L G H V A Q V L M    17
M Q L R N P K L H L G C A L A L R F L A L V S V D I P G A R A    31
                    M F A F Y F L T A C I S L K G V F G    18

R D A S G R L M P D P K R F P H G I P F L A D Y I V H S L G L K L    116
- - - - - - - - - - - - - - - - - - - - - - - - - - - - - - - -
R D S E G R L Q A D P Q R F P H G I R Q L A N Y I V H S K G L K L    131
- * * * - - - - - * - - - - * - - - - - - - - - - - - - - - - -
R D S D G F L V A D E Q K F P N G M G H V A D H L H N N S F L F    107
                                    415
A F S C S V P A Y E G G L P P R I V N Y S L L A D I C N L W R N Y    215
- - - - - - - - - - - - - - - - - - - - - - - - - - - - - - -
V Y S C C E W P L Y M W P F   Q K P N Y T E I R Q Y C N H W R N F    229
- * * - - - - - - - - - - - - - - - - - - - - - - - - - - - - -
F Y S C N W G L Y G S G I A N     S W R M S G D V T A E F T R P    204
                    221

S T D L R T I S A Q N M D I L Q N P L M I K I N Q D P L G I Q G    315
- - - - - - - - - - - - - - - - - - - - - - - - - - - - - - -
S N D L R H I S P Q A K A L L Q D K D V I A I N Q D P L G K Q G    328
- - * * - - - - - - - - - - - - - - - * - - - - - - - - - - - -
G A N V N N L K A S S Y S I Y S Q A S V I A I N Q D S N G I P A    302
                                    -
Y G N V R N    349           363    E V A C L V D A N G I Q P    375

G L R D E T N   F T V I I N P S G V V M W Y L Y P I K N L E M S Q Q    411
- - - - - - - - - - - - - - - - - - - - - - - - - - - - - - - -
G F Y E W T S R L R S H I N P T G T V L L Q L E N T M N M S L K D L L    429
- * * - - - - - - - - - - - - - - - - - - - - - - - - - - - - - -
G L Y E I Y K D G L K N R L G Q K G S L I L N V P A H I A F R L R P S S    404
  213                        241
```

CONT.
FROM

CONT. ON FIG. 5B

```
                     947    957
          Sense    5'-GGATTCACAAGGAAA-3'
                        929    919
          Antisense 5'-GCCTAAGGGATCCTGGTTG-3'
                                940   919
          Antisense 5'-CGTCCCTGGATGCCTAAGGGATCCTGGTTG-3'
                                     950
          Antisense 5'-GTGAATCCTGCGTCCC
                                          Sense 5'-CAACC      CONT.
                                                              ON
                          Exon 6 ←---- 70 bp Insert ----→
pcD-HS1204 5'-GGATTCACAAGGGATCCTGGATGCCTAAGGGATCCTGCGTCCC
                          ←---- 45 bp Deletion ----
pAGB-13    5'-GGATTCACAAGGAAAAATCTCTCATCGAAGTGTACATGCGGCC
                          Exon 6 | Exon 7
```

```
                                * *         ***
760  CTG CTC ATT GGG AAC TTT GGT CTC AGC TTA GAG CAA TCC CGG GCC
     Leu Leu Ile Gly Asn Phe Gly Leu Ser Leu Glu Gln Ser Arg Ala

849  ACA GAC CTG CGT ACC ATC TCC GCC CAG AAC ATG GAC ATT CTG CAG
     Thr Asp Leu Arg Thr Ile Ser Ala Gln Asn Met Asp Ile Leu Gln

                          *   *       ***
939  GGA CGC AGG ATT CAC AAG|gtactagggtgtggagggaaggaaggggagggctg
     Gly Arg Arg Ile His Lys|
                      Exon 6|
     tacaggagtcgcccagtccccaaccagggctaccccttctggttgcttatggttgagga
     acagctcaagggagtcggggatgagaggtgtcagccacataagtgcacatagcaagggt
     gcaggaggagctggtttgtttgttttgagacagggtctcactctgtcacccaggctgg
     gtgcctcagcctcctgagtagctggcactacaggcgcctgcaccacacccagctaattt
     gatccacccgtatcagcctcccaaagtgctgggattacaggcatgagcaccgcactcgg
     tacctaccatgtgctgggagttttagataatttttctcagcaaggtagttatcttgcca
     agttggtacaaacaagactggacttcagtgtcacctcaaagccttttttttttttttt
     cactgcaacctctggctcccaggttcaagcgatttcctgcctcagcctcccaggtagc
     gacagggtttcaccatgttggccaggctactctcaaaactcctgacgtcagctgatcca
     gctctttaccaaatcctggattctggtaaaaagaaacctacagaactatggaaggcacc
     gctgggcctggaaaccttctggaggatgggagttcacatccagctccactctccaccc
     gtttggggccagcactcatacgctgtactgttgttgcgcttccctgtttctgcgtttat
     tagcatagggggccgggctcagagtaggtgttgatgagtatctgctgagtcagggaaggt
                   *
958  tgtgacatggagctgtgaactggggacccagaactcagggaggccagggaggcaatg

               *                          *       **
964  TCT CTC ATC GAA GTG TAC ATG CGG CCT CTG TCC AAC AAG|GCT AGC
     Ser Leu Ile Glu Val Tyr Met Arg Pro Leu Ser Asn Lys|Ala Ser
                                                        |Exon 7 - pAGB-13
```

CONT. ON FIG. 5D

FIG. 5C

CONT. FROM FIG5C

```
CAG ATG GCC CTG TGG ACG GTG CTG GCA GCC CCC CTC TTG ATG TCC  848
Gln Met Ala Leu Trp Thr Val Leu Ala Ala Pro Leu Leu Met Ser

AAT CCA CTC ATG ATC AAA ATC AAC CAG GAT CCC TTA GGC ATC CAG  938
Asn Pro Leu Met Ile Lys Ile Asn Gln Asp Pro Leu Gly Ile Gln

aggaactgggttctcctgagagaaaggctgccagctccctgggggcaacacctggcgagg  957

ctctgatgggagctgctccaactgtcctcctcttgctgggtgagagcagggctgagcagg
gaggcacagagcttctatacacccgtgatggcctgcagagagcttggacttccctccaga
agtgcagtggcacaatttcgactcactgcaatctctacctgccaggttcaagcaattctc
ttgtattttagtagagacaccatgttggccaggcttgtctcgaactcctggcctcaggt
ccaggagaagctgttatagccaaggaatactacgactactggtggctgctatttattgag
ttttacaaatgagaaaaatgaaacttcgagagtctgagtaactttatcccaaggctacac
tttttgagatggagtctcacgctgtagcccaggctggagtgcagtggcaccatctcagct
tgggattacaggtgtgcgccaccacacccggctaatttttttgtatttttttcagtaga
ctgcctcggcctcacaaagtaatgggattacagcatgagccactgtgcctgtctgccttt
tatagaactggtgatgcccagaggaagtaacaattccctgccagaggggctgatggtgga
tcctggaacagagttcactgttcccactggacagcaccctccaggccagcactggcagct
ccctcccgttgtcctatgagcttctggggcagggctcatgcagcacttgtctcagtgtgc
gggcagatagggttagataagctggggtgctggaggcccgtgcgatcctccctaaacctg
                                            *  *
gtaggtcctgtctgagcaagggaccccagccagtagccaccttctgtgcccag|GAA AAA  963
                                                     |Glu Lys
                                                     |Exon 7

GCC TTA GTC TTC TTC AGC TGC AGG ACC GAT ATG CCT TAT CGC TAC 1053
Ala Leu Val Phe Phe Ser Cys Arg Thr Asp Met Pro Tyr Arg Tyr
```

FIG.5D

CLONING AND EXPRESSION OF BIOLOGICALLY ACTIVE α-N-ACETYLGALACTOSAMINIDASE

TABLE OF CONTENTS

1. Introduction . . .
2. Background of the Invention . . .
2.1. α-GalNAc And Schindler Disease . . .
2.2. Lysosomal Enzymes: Biosynthesis And Targeting . . .
3. Summary of the Invention . . .
3.1. Definition . . .
4. Description of the Figures . . .
5. Detailed Description of the Invention . . .
5.1. The α-GalNAc Coding Sequence . . .
5.2. Expression Of α-GalNAc . . .
5.2.1. Construction Of Expression Vectors And Preparation Of Transfectants . . .
5.2.2. Identification Of Transfectants Or Transformants Expressing The α-GalNAc Gene Product . . .
5.2.3. Purification Of The α-GalNAc Gene Product . . .
5.2.4. Modified Glycoforms Of Recombinant α-GalNAc . . .
5.3. Uses Of The Recombinant α-GalNAc . . .
6. Example: Cloning And Expression Of Biologically Active α-GalNAc . . .
6.1. Materials And Methods . . .
6.1.1. Affinity Purification, Microsequencing And Antibody Production . . .
6.1.2. Construction Of Synthetic Oligonucleotide Probes . . .
6.1.3. Isolation And Characterization Of cDNA and Genomic Clones . . .
6.1.4. DNA Sequencing And Computer-Assisted Analyses . . .
6.1.5. Transient Expression Assays . . .
6.1.6. Northern Hybridization And Cap Site Analyses . . .
6.1.7. Construction Of p91α-GalA6/α-GalNAc7 . . .
6.1.8. Primer Extension And PCR Amplification Of cDNA And Genomic Sequences . . .
6.2. Results . . .
6.2.1. Purification And Characterization Of Human α-GalNAc . . .
6.2.2. Isolation, Characterization And Expression Of A Full-Length cDNA . . .
6.2.3. Northern Hybridization And Cap-Site Analyses . . .
6.2.4. Sequence Homology Between α-GalNAc And α-Gal A . . .
6.2.5. Primer Extension And PCR And Sequence Analyses Of cDNA And Genomic Sequences . . .
7. Deposit Of Microorganisms . . .

This work was supported in part by a grant from the National Institutes of Health and a grant from the March of Dimes Birth Defects Foundation.

1. INTRODUCTION

The present invention relates to the production of biologically active human α-GalNAc, involving cloning and expression of the genetic coding sequence of α-GalNAc in eukaryotic expression systems which provide for proper posttranslational modifications and processing of the expression product.

The α-GalNAc so produced may be used in enzyme replacement therapy for Schindler Disease, or in the hydrolysis of α-N-acetylgalactosaminyl moieties from various glycoconjugates, such as the conversion of blood Group A erythrocytes to cells with the O blood group antigen.

2. BACKGROUND OF THE INVENTION

In the early 1970's, several investigators demonstrated the existence of two α-Galactosidase isozymes designated A and B, which hydrolyzed the α-galactosidic linkages in 4-MU- and/or ρ-NP-α-D-galactopyranosides (Kint, 1971, Arch. Int. Physiol. Biochem. 79: 633–644; Beutler & Kuhl, 1972, Amer. J. Hum. Genet. 24: 237–249; Romeo, et al., 1972, FEBS Lett. 27: 161–166; Wood & Nadler, 1972, Am. J. Hum. Genet. 24: 250–255; Ho, et al., 1972, Am. J. Hum. Genet. 24: 256–266; Desnick, et al., 1973, J. Lab. Clin. Med. 81: 157–171; and Desnick, et al., 1989, in The Metabolic Basis of Inherited Disease, Scriver, C. R., Beaudet, A. L. Sly, W. S. and Valle, D., eds, pp. 1751–1796, McGraw Hill, New York). In tissues, about 80%–90% of total α-Galactosidase (α-Gal) activity was due to a thermolabile, myoinositol-inhibitable α-Gal A isozyme, while a relatively thermostable, α-Gal B, accounted for the remainder. The two "isozymes" were separable by electrophoresis, isoelectric focusing, and ion exchange chromatography. After neuraminidase treatment, the electrophoretic migrations and pI value of α-Gal A and B were similar (Kint, 1971; Arch. Int. Physiol. Biochem. 79: 633–644), initially suggesting that the two enzymes were the differentially glycosylated products of the same gene. The finding that the purified glycoprotein enzymes had similar physical properties including subunit molecular weight (~46 kDa), homodimeric structures, and amino acid compositions also indicated their structural relatedness (Beutler & Kuhl, 1972, J. Biol. Chem. 247: 7195–7200; Callahan, et al., 1973, Biochem. Med. 7: 424–431; Dean, et al., 1977, Biochem. Biophys. Res. Comm. 77: 1411–1417; Schram, et al., 1977, Biochim. Biophys. Acta. 482: 138–144; Kusiak, et al., 1978, J. Biol. Chem. 253: 184–190; Dean, et al., 1979, J. Biol. Chem. 254: 10001–10005; and Bishop, et al., 1980, in Enzyme Therapy in Genetic Disease:2, Desnick, R. J., ed., pp. 17–32, Alan R. Liss, Inc., New York). However, the subsequent demonstration that polyclonal antibodies against α-Gal A or B did not cross-react with the other enzyme (Beutler & Kuhl, 1972, J. Biol. Chem. 247: 7195–7200; and Schram, et al., 1977, Biochim. Biophys. Acta. 482: 138–144), that only α-Gal A activity was deficient in hemizygotes with Fabry disease (Kint, 1971, Arch. Int. Physiol. Biochem. 79: 633–644; Beutler & Kuhl, 1972, Amer. J. Hum. Genet. 24: 237–249; Romeo, et al., 1972, FEBS Lett. 27: 161–166; Wood & Nadler, 1972, Am. J. Hum. Genet. 24: 250–255; Ho, et al., 1972, Am. J. Hum. Genet. 24: 256–266; Desnick, et al., 1973, J. Lab. Clin. Med. 81: 157–171; Desnick, et al., 1989, in The Metabolic Basis of Inherited Disease, Scriver, C. R., Beaudet, A. L. Sly, W. S. and Valle, D., eds, pp. 1751–1796, McGraw Hill, New York; and, Beutler & Kuhl, 1972, J. Biol. Chem. 247: 7195–7200); and that the genes for α-Gal A and B mapped to different chromosomes (Desnick, et al., 1989, in The Metabolic Basis of Inherited Disease, Scriver, C. R., Beaudet, A. L. Sly, W. S. and Valle, D., eds, pp. 1751–1796, McGraw Hill, New York; deGroot, et al., 1978, Hum. Genet. 44: 305–312), clearly demonstrated that these enzymes were genetically distinct.

2.1. α-GalNAc AND SCHINDLER DISEASE

In 1977 α-Gal B was shown to be an α-N-acetylgalactosaminidase (α-GalNAc), a homodimeric glycoprotein which hydrolyzed artificial and natural substrates with terminal α-N-acetylgalactosaminyl moieties (Dean, et al., 1977, Biochem. Biophys. Res. Comm. 77: 1411–1417; Schram, et al., 1977, Biochim. Biophys. Acta. 482: 138–144; and, Bishop, et al., 1980, in Enzyme Therapy in Genetic Disease:2, Desnick, R. J., ed., pp. 17–32, Alan R. Liss, Inc., New York) including various O- and N-linked glycopeptides and glycoproteins, glycosphingolipids, and the proteoglycan, cartilage keratin sulfate II (Desnick, et al., 1989, in The Metabolic Basis of Inherited Disease, Scriver, C. R., Beaudet, A. L. Sly, W. S. and Valle, D., eds, pp. 1751–1796, McGraw Hill, New York).

Purified α-GalNAc has reported native and subunit molecular weights of 90 to 117 kDa and 46 to 48 kDa, respectively (Beutler & Kuhl, 1972, J. Biol. Chem. 247: 7195–7200; Callahan, et al., 1973, Biochem. Med. 7: 424–431; Dean, et al., 1977, Biochem. Biophys. Res. Comm. 77: 1411–1417; Schram, et al., 1977, Biochim. Biophys. Acta. 482: 138–144; Kusiak, et al., 1978, J. Biol. Chem. 253: 184–190; Dean, et al., 1979, J. Biol. Chem. 254: 10001–10005; and, Bishop, et al., 1980, in Enzyme Therapy in Genetic Disease:2, Desnick, R. J., ed., pp. 17–32, Alan R. Liss, Inc., New York). Kinetic studies demonstrated that the enzyme was inhibited by α-N-acetylgalactosamine ($K_i$~2.1 mM) and hydrolyzed synthetic substrates with either terminal α-N-acetylgalactosaminide ($K_m$~1–2 mM) or α-D-galactoside moieties ($K_m$~7–10 mM) (Beutler & Kuhl, 1972, J. Biol. Chem. 247: 7195–7200; Callahan, et al., 1973, Biochem. Med. 7: 424–431; Dean, et al., 1977, Biochem. Biophys. Res. Comm. 77: 1411–1417; Schram, et al., 1977, Biochim. Biophys. Acta. 482: 138–144; Kusiak, et al., 1978, J. Biol. Chem. 253: 184–190; Dean, et al., 1979, J. Biol. Chem. 254: 10001–10005; and, Bishop, et al., 1980, in Enzyme Therapy in Genetic Disease:2, Desnick, R. J., ed., pp. 17–32, Alan R. Liss, Inc., New York). Biosynthetic studies performed with cultured fibroblasts indicated that the human enzyme was synthesized as a 65 kDa glycosylated precursor which was processed to a mature 48 kDa lysosomal form; both the precursor and mature forms had high-mannose type oligosaccharide chains, but only the precuror's mannose residues were phosphorylated (Sweeley, et al., 1983, Arch. Biochim. Biophys. 223: 158–165).

The deficient activity of α-GalNAc was demonstrated in two brothers with Schindler disease (van Diggelen, et al., 1988, J. Inher. Met. Dis. 11: 349–357; Schindler, et al., 1989, N. Engl. J. Med. 320: 1735–1740), a newly recognized form of infantile neuroaxonal dystrophy (Schindler, et al., 1989, N. Engl. J. Med. 320: 1735–1740). The affected brothers excreted increased amounts of O-linked glycopeptides and oligosaccharides containing α-N-acetylgalactosaminyl moieties which were detectable in urinary screening profiles (van Diggelen, et al., 1988, J. Inher. Met. Dis. 11: 349–357; Schindler, et al., 1990, Clin. Chim. Acta 190: 81–92; Schindler, et al. 1989, N. Engl. J. Med. 320: 1735–1740). Biochemical and immunologic studies revealed that neither α-GalNAc activity or enzyme protein was present in fibroblast lysates from the affected sibs (Schindler, et al., 1989, N. Engl. J. Med. 320:

1735–1740). Thus, efforts were undertaken to isolate and express a full-length α-GalNAc cDNA in order to determine the nature of the molecular lesions in patients with Schindler disease, and to characterize the genomic organization and expression of the human gene encoding this lysosomal hydrolase.

While expression studies of a hybrid α-GalNAc sequence were in progress, Tsuji, S., et al. (1989, Biochem. Biophys. Res. Comm. 163: 1498–1504), reported the isolation of a human α-GalNAc cDNA. Unlike the full-length pAGB-3 α-GalNAc cDNA sequence reported herein, the Tsuji et al. clone, pcD-HS1204, contained a 70 bp insertion after pAGB-3 nt 957 which altered the reading frame for pAGB-3 residues 330 to 411 and resulted in a truncated polypeptide of only 358 residues. Although their predicted amino acid sequence did not include the tryptic peptide described herein containing residues 335 to 344, we investigated whether the 70 bp insertion may have resulted from alternative splicing. The results reported herein demonstrate the isolation, nucleotide sequence and transient expression of a full-length cDNA encoding α-GalNAc. Genomic sequencing did not reveal the presence of the putative 70 bp insertion, thereby affirming that the expressible pAGB-3 transcript is authentic. In addition, remarkable homology between the predicted α-GalNAc and α-Gal A amino acid sequences was identified, suggesting the evolutionary relatedness of the autosomal and X-linked genes encoding these lysosomal hydrolases.

2.2. LYSOSOMAL ENZYMES: BIOSYNTHESIS AND TARGETING

Lysosomal enzymes are synthesized on membrane-bound polysomes in the rough endoplasmic reticulum. Each protein is synthesized as a larger precursor containing a hydrophobic amino terminal signal peptide. This peptide interacts with a signal recognition particle, an 11S ribonucleoprotein, and thereby initiates the vectoral transport of the nascent protein across the endoplasmic reticulum membrane into the lumen (Erickson, et al., 1981, J. Biol. Chem. 256: 11224; Erickson, et al., 1983, Biochem. Biophys. Res. Commun. 115: 275; Rosenfeld, et al., 1982, J. Cell Biol. 93: 135). Lysosomal enzymes are cotranslationaly glycosylated by the en bloc transfer of a large preformed oligosaccharide, glucose-3, mannose-9, N-acetylglucosamine-2, from a lipid-linked intermediate to the Asn residue of a consensus sequence Asn-X-Ser/Thr in the nascent polypeptide (Kornfeld, R. & Kornfeld, S., 1985, Annu. Rev. Biochem. 54: 631). In the endoplasmic reticulum, the signal peptide is cleaved, and the processing of the Asn-linked oligosaccharide begins by the excision of three glucose residues and one mannose from the oligosaccharide chain.

The proteins move via vesicular transport to the Golgi stack, where they undergo a variety of posttranslational modifications, and are sorted for proper targeting to specific destinations: lysosomes, secretion, plasma membrane. During movement through the Golgi, the oligosaccharide chain on secretory and membrane glycoproteins is processed to the sialic acid-containing complex-type. While some of the oligosaccharide chains on lysosomal enzymes undergo similar processing, most undergo a different series of modifications. The most important modification is the acquisition of phosphomannosyl residues which serve as an essential component in the process of targeting these enzymes to the lysosome (Kaplan, et al., 1977, Proc. Natl. Acad.

Sci. USA 74: 2026). This recognition marker is generated by the sequential action of two Golgi enzymes. First, N-acetylglucosaminylphosphotransferase transfers N-acetylglucosamine-1-phosphate from the nucleotide sugar uridine diphosphate-N-acetylglucosamine to selected mannose residues on lysosomal enzymes to give rise to a phosphodiester intermediate (Reitman & Kornfeld, 1981, J. Biol. Chem. 256: 4275; Waheed, et al., 1982, J. Biol. Chem. 257: 12322). Then, N-acetylglucosamine-1-phosphodiester α-N-acetylglucosaminidase removes the N-acetylglucosamine residue to expose the recognition signal, mannose-6-phosphate (Varki & Kornfeld, 1981, J. Biol. Chem. 256: 9937; Waheed, et al., 1981, J. Biol. Chem. 256: 5717).

Following the generation of the phosphomannosyl residues, the lysosomal enzymes bind to mannose-6-phosphate (M-6-P) receptors in the Golgi. In this way the lysosomal enzymes remain intracellular and segregate from the proteins which are destined for secretion. The ligand-receptor complex then exits the Golgi via a coated vesicle and is delivered to a prelysosomal staging area where dissociation of the ligand occurs by acidification of the compartment (Gonzalez-Noriega, et al., 1980, J. Cell Biol. 85: 839). The receptor recycles back to the Golgi while the lysosomal enzymes are packaged into vesicles to form primary lysosomes. Approximately, 5–20% of the lysosomal enzymes do not traffic to the lysosomes and are secreted, presumably, by default. A portion of these secreted enzymes may be recaptured by the M-6-P receptor found on the cell surface and be internalized and delivered to the lysosomes (Willingham, et al., 1981, Proc. Natl. Acad. Sci. USA 78: 6967).

Two mannose-6-phosphate receptors have been identified. A 215 kDa glycoprotein has been purified from a variety of tissues (Sahagian, et al., 1981, Proc. Natl. Acad. Sci. USA, 78: 4289; Steiner & Rome, 1982, Arch. Biochem. Biophys. 214: 681). The binding of this receptor is divalent cation independent. A second M-6-P receptor also has been isolated which differs from the 215 kDa receptor in that it has a requirement for divalent cations. Therefore, this receptor is called the cation-dependent (M-6-P$^{CD}$) while the 215 kDa one is called cation-independent (M-6-P$^{CI}$). The M-6-P$^{CD}$ receptor appears to be an oligomer with three subunits with a subunit molecular weight of 46 kDa.

3. SUMMARY OF THE INVENTION

The present invention involves the production of human α-GalNAc by cloning and expressing the α-GalNAc coding sequence in eukaryotic host cell expression systems. The eukaryotic expression systems, and in particular the mammalian host cell expression systems described herein, provide for stable and high level expression of α-GalNAc, as well as appropriate co-translational and post-translational modifications required for proper processing, e.g., glycosylation, phosphorylation, etc. and sorting of the expression product so that an active enzyme is produced. Also described is the engineering of α-GalNAc fusion proteins which are readily purified. These fusion proteins are engineered so that the α-GalNAc moiety is readily cleaved from the fusion protein and recovered.

The α-GalNAc produced in accordance with the invention may be used for a variety of ends, including but not limited to the treatment of Schindler disease; the hydrolyses of α-N-acetylgalactosaminyl moieties from glycoproteins, glycopeptides, glycolipids and other glycoconjugates; and for the conversion of the human A blood group determinant on erythrocytes to the O-blood group antigen.

3.1. DEFINITIONS

As used herein, the following terms and abbreviations will have the indicated meaning:

| | |
|---|---|
| α-Galactosidase A | α-Gal A |
| α-N-Acetylgalactosaminidase | α-GalNAc |
| base pair(s) | bp |
| Chinese hamster ovary | CHO |
| complementary DNA | cDNA |
| counts per minute | cpm |
| deoxyribonucleic acid | DNA |
| Dulbecco's Modified Eagle's Medium | DMEM |
| fetal calf serum | FCS |
| hour(s) | hr |
| kilobase pairs | kb |
| kilodalton | kDa |
| mannose-6-phosphate | M-6-P |
| methotrexate | MTX |
| 4-methylumbelliferyl-α-D-galactoside | 4-MU-α-Gal |
| 4-methyl-umbelliferyl-α-N-acetylgalactosaminide | 4-MU-α-GalNAc |
| micrograms | μg |
| nanograms | ng |
| nucleotide | nt |
| p-nitrophenyl-α-N-acetylgalactosaminide | pNP-α-GalNAc |
| polyacrylamide gel electrophoresis | PAGE |
| polymerase chain reaction | PCR |
| ribonucleic acid | RNA |
| riboprobe for α-GalNAc | rb-AGB-3 |
| sodium dodecyl sulfate | SDS;NaDodSO$_4$ |
| units | U |

4. DESCRIPTION OF THE FIGURES

Figure 1B:
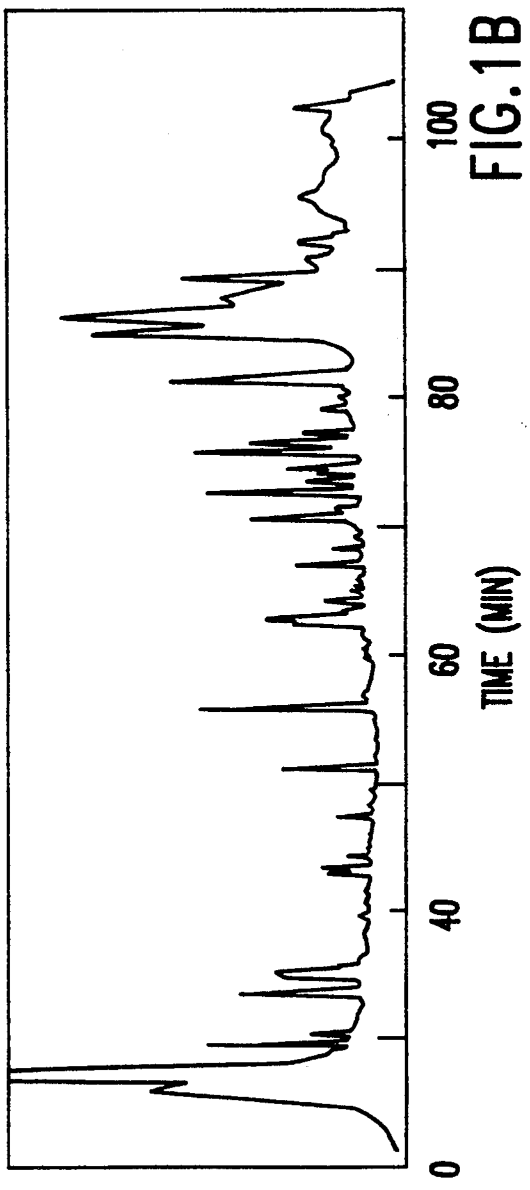
Figure 1C:
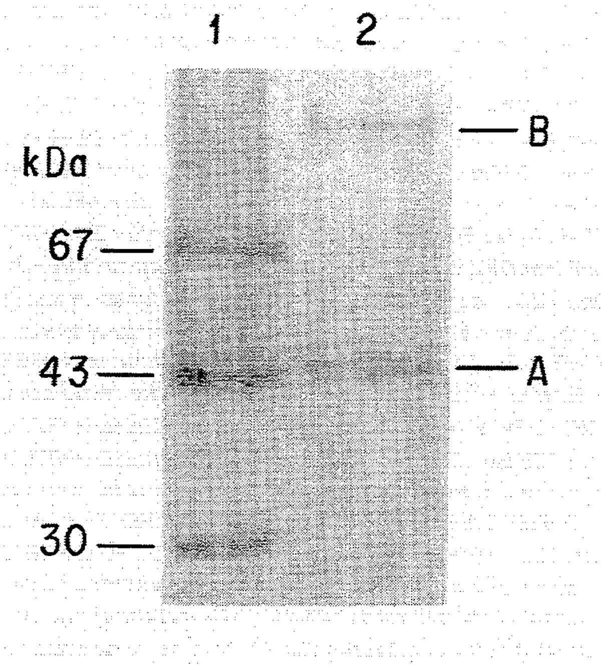

FIG. 1A–FIG. 1C Reversed-phase HPLC separation of tryptic peptides from electroeluted 117 kDa (FIG. 1A) and 48 kDa (FIG. 1B) species of purified human α-GalNAc. The indicated peptides were microsequenced. (FIG. 2C) NaDodSO$_4$/PAGE of purified α-GalNAc.

FIG. 2A–FIG. 2D Nucleotide and predicted amino acid sequences of the pAGB-3 cDNA insert containing the complete coding region for human α-GalNAc [SEQ ID NOS 1 & 2]. The A of the initiation ATG is nt 1 and the N-terminal Met of the signal peptide is amino acid 1. Bold underlines indicate colinear amino acid sequence obtained by microsequencing the N-terminal (N-ter) and tryptic peptides (T) of the purified enzyme. CHO indicates potential sites of N-glycosylation. Overlines indicate the polyadenylation signal (AATAAA) and the pentanucleotide sequence (CACTG) recognized by the U4 small nuclear ribonucleoprotein.

Figure 3:
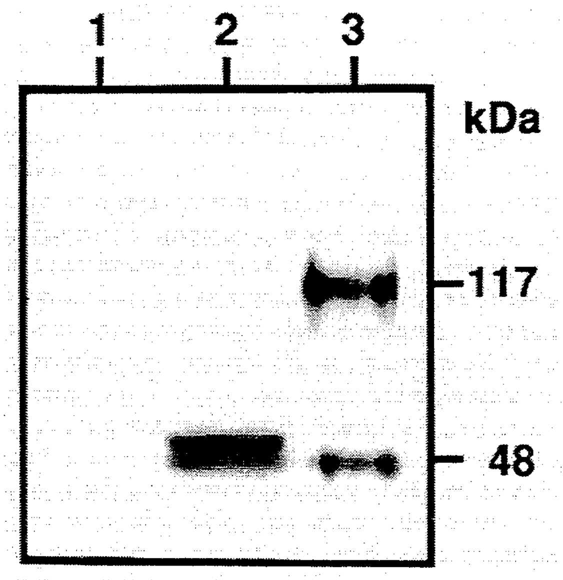

FIG. 3 Immunoblot of human α-GalNAc expressed in COS-1 cells. Lanes: 1, mock-transfection; 2, p91-AGB-3 transfection; 3, purified human lung α-GalNAc.

FIG. 4A–FIG. 4C Alignment of amino acid sequences deduced from the full-length cDNAs encoding human α-GalNAc (α-Gal B) [SEQ ID NO: 2], α-Gal A [SEQ ID NO: 3], yeast Mel 1 [SEQ ID NO: 4], and *E. coli* Mel A [SEQ ID NOS: 5–7]. Colons, identical residues; single dots, isofunctional amino acids; and boxes, identical residues in α-GalNAc, α-Gal A, Mel 1 and/or Mel A. Gaps were introduced for optimal alignment. Numbered vertical lines indicate exon boundaries for α-Gal A (Bishop, et al., 1988, Proc. Natl. Acad. Sci. USA 85: 3903–3907).

Figure 5A:
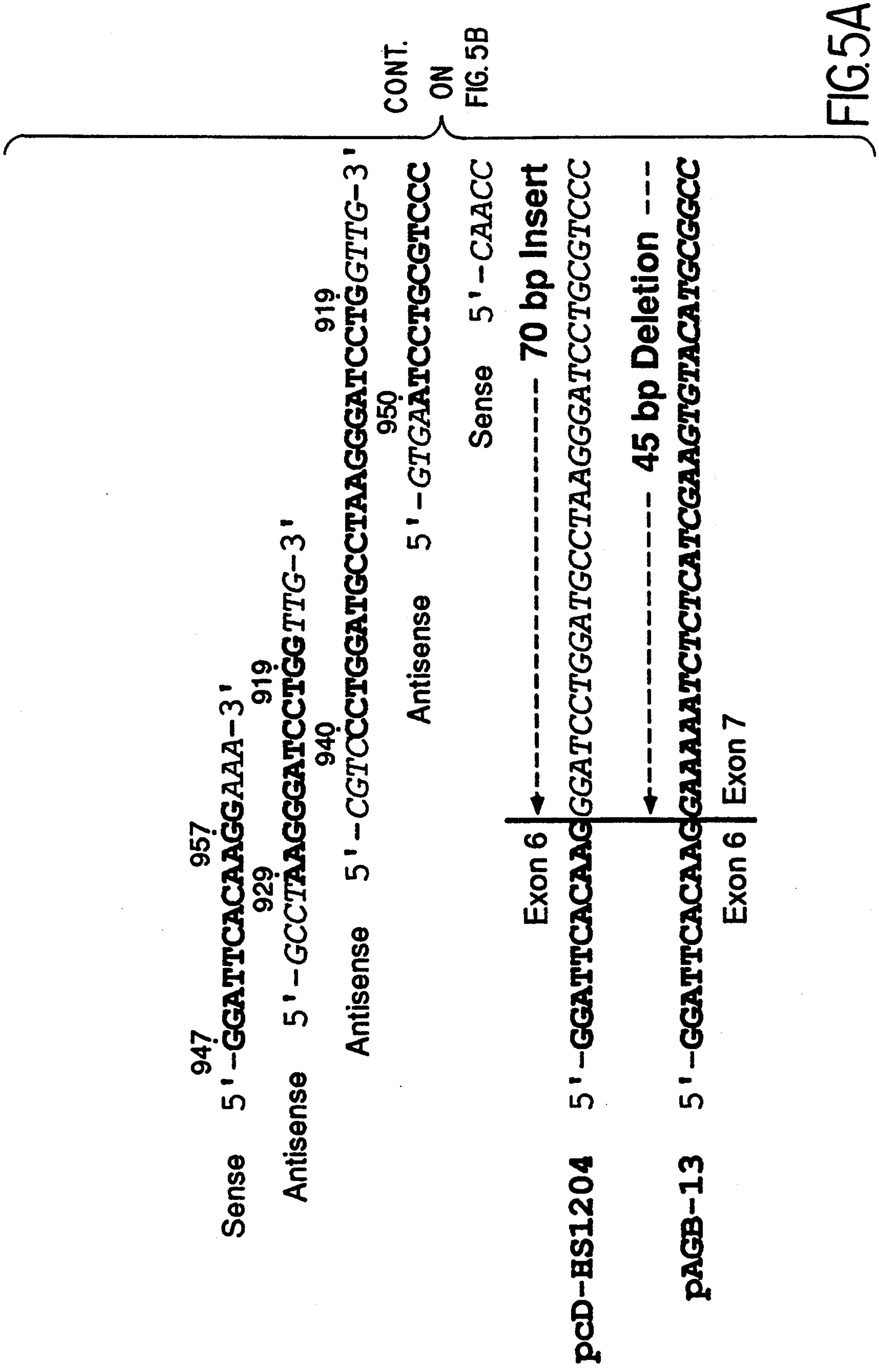
Figure 5B:
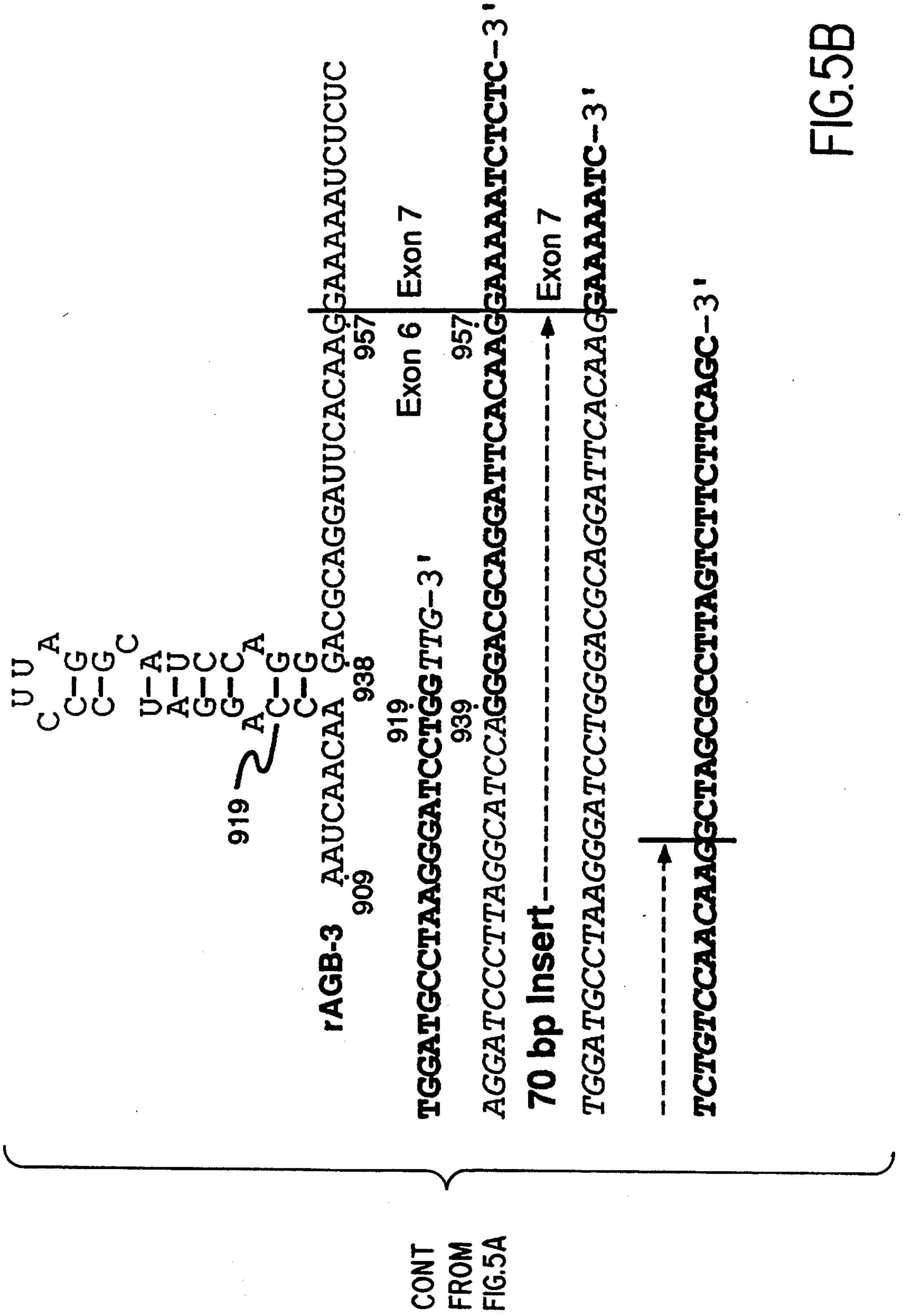

FIG. 5A–FIG. 5D Partial genomic sequence of human α-GalNAc including an intron between coding nt 957 and 958. FIG. 5B: rb-AGB-3: partial α-GalNAc RNA sequence (nt 909 to 969) corresponding to the 3' end of α-Gal A exon 6 [SEQ ID NO: 8] (Bishop, et al., 1988, Proc. Natl. Acad. Sci. USA 85: 3903–3907). The indicated stem and loop structure between nt 918 and 937 had a ΔG of −11.6 (Zuker, 1989, Methods Enzymol. 180: 262–288). The overlapped antisense [SEQ ID NO: 9] and sense [SEQ ID NO: 1] sequences shown in bold are inverted and direct repeats derived from nt 919 to 957 of pAGB-3 that are in the 70 bp insertion of pcD-HS1204 [SEQ ID NO: 10] (Tsuji, S., et al., 1989, Biochem. Biophys. Res. Comm. 163: 1498–1504). The 45 bp deletion in clone pAGB-13 is indicated in italics. FIG. 5C–FIG. 5D: The genomic α-GalNAc sequence from coding nt 760 to 1053 (upper case) includes a 1754 nt intron between nt 959 and 958 which corresponds in position to the α-Gal A exon 6 and 7 boundaries [SEQ ID NO: 11]. Dashed line, the 5' splice donor sequence; solid underlines, putative branch point sequences; dotted underlines, putative polypyrimidine tracts at the 3' acceptor sites for the normal gene and mutant pAGB-13; and asterisks, differences from the consensus sequence (Reed & Maniatis, 1988, Genes Dev. 2: 1268–1276).

5. DETAILED DESCRIPTION OF THE INVENTION

The present invention relates to the production of biologically active human α-GalNAc involving cloning and expressing the nucleotide coding sequences for the enzyme in eukaryotic expression systems. Successful expression and production of this purified, biologically active enzyme as described and exemplified herein is particularly significant for a number of reasons. For example, past efforts to express the full-length cDNA encoding α-Gal A using various prokaryotic expression vectors resulted in expression of the enzyme, as evidenced by enzyme assays of intact microbial host cells and growth on melibiose as the carbon source; however, the human enzyme was expressed at low levels and could not be purified from the bacteria. These results indicate that the recombinant enzyme expressed in microbial systems was unstable due to the lack of normal glycosylation and/or the presence of endogenous cytoplasmic or periplasmic proteases. These studies also suggest that the homologous α-GalNAc glycoprotein also would not be expressable in bacteria.

The expression of these enzymes in eukaryotic expression systems are equally difficult for different reasons. The α-Gal A and α-GalNAc are lysosomal enzymes encoded by "housekeeping" genes. The primary translation product is highly modified and processed involving a complex series of events including cleavage of a signal sequence, glycosylation, and phosphorylation which can be properly effected only by appropriate host cells. Moreover, since the expression product is destined for the lysosome, which remains intracellular, it is quite surprising that the methods described herein allow for the secretion of a properly processed, biologically active molecule.

The biologically active α-GalNAc produced in accordance with the invention has a variety of uses, probably the most significant being its use in enzyme replacement therapy for the lysosomal storage disorder Schindler's disease. However, large quantities of biologically active α-GalNAc which do not induce an immune response are required for replacement therapy. Such quantities of active enzyme have not heretofore been obtained. In addition, the enzyme can be used for hydrolysis of the α-N-acetylgalactosaminyl residues from various glycoconjugates, and for the modification of the A-blood group on erythrocytes to the O-blood group antigenic type.

The invention is divided into the following sections solely for the purpose of description: (a) the coding sequence for α-GalNAc; (b) construction of an expression vector which will direct the expression of the enzyme coding sequences; (c) transfection of appropriate host cells which are capable of replicating, translating and properly processing the primary transcripts in order to express a biologically active gene product; and (d) identification and/or purification of the enzyme so produced. Once a transformant is identified that expresses high levels of biologically active enzyme, the practice of the invention involves the expansion and use of that clone in the production of purified, biologically active α-GalNAc.

The invention is demonstrated herein, by way of examples in which cDNAs of α-GalNAc were cloned and expressed in a mammalian expression system. Modifications to the cDNA coding sequences which improve yield, and simplify purification without detracting from biological activity are also described.

Various aspects of the invention are described in more detail in the subsections below and in the examples that follow.

5.1. The α-GalNAc CODING SEQUENCE

The nucleotide coding sequence and deduced amino acid sequence for α-GalNAc is depicted in FIG. 2A–FIG. 2D [SEQ ID NOS: 1 & 2]. This nucleotide sequence, or fragments or functional equivalents thereof, may be used to generate recombinant DNA molecules that direct the expression of the enzyme products, or functionally active peptides or functional equivalents thereof, in appropriate host cells.

Due to the degeneracy of the nucleotide coding sequences, other DNA sequences which encode substantially the same amino acid sequence as depicted in FIG. 2A–2D may be used in the practice of the invention for the cloning and expression of α-GalNAc. Such alterations include deletions, additions or substitutions of different nucleotide residues resulting in a sequence that encodes the same or a functionally equivalent gene product. The gene product may contain deletions, additions or substitutions of amino acid residues within the sequence, which result in a silent change thus producing a bioactive product. Such amino acid substitutions may be made on the basis of similarity in polarity, charge, solubility, hydrophobicity, hydrophilicity, the amphipathic nature of the residues involved, and/or on the basis of crystallographic data. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; and phenylalanine, tyrosine.

The coding sequence for α-GalNAc may be conveniently obtained from genetically engineered microorganisms or cell lines containing the enzyme coding sequences, such as the deposited embodiments described herein. Alternatively, genomic sequences or cDNA coding sequences for these enzymes may be obtained from human genomic or cDNA libraries. Either genomic or cDNA libraries may be prepared from DNA fragments generated from human cell sources. The fragments which encode α-GalNAc may be identified by screening such libraries with a nucleotide probe that is substantially complementary to any portion of the sequences depicted in FIG. 2A–FIG. 2D. Indeed, sequences generated by polymerase chain reaction can be ligated to form the full-length sequence. Although portions of the coding sequences may be utilized, full length clones, i.e., those containing the entire coding region for α-GalNAc, may be preferable for expression. Alternatively, the coding sequences depicted in FIG. 2A–FIG. 2D may be altered by the addition of sequences that can be used to increase levels of expression and/or to facilitate purification. For example, the α-GalNAc coding sequence could be modified by the addition of the nucleotide sequence encoding the cleavage site for collagenase followed by the Staphylococcal Protein A sequence. Expression of this chimeric gene construct would result in a fusion protein consisting of α-GalNAc, the collagenase substrate and Protein A. This fusion protein may be readily purified using an IgG column which binds to the Protein A moiety. Unfused α-GalNAc may be released from the column by treatment with collagenase which cleaves the α-GalNAc from the Protein A moiety bound to the column. Other enzyme cleavage substrates and binding proteins can be engineered into similar constructs for the production of α-GalNAc which can be readily purified and released in its biologically active form.

Techniques well-known to those skilled in the art for the isolation of DNA, generation of appropriate restriction fragments, construction of clones and libraries, and screening recombinants may be used. For a review of such techniques, see, for example, Sambrook, et al., 1989, Molecular Cloning A Laboratory Manual, 2nd Ed., Cold Spring Harbor Press, N.Y., Chapters 1–18.

In an alternate embodiment of the invention, the coding sequence of FIG. 2A–FIG. 2D could be synthesized in whole or in part, using chemical methods well-known in the art. See, for example, Caruthers, et al., 1980, Nuc. Acids Res. Symp. Ser. 7: 215–233; Crea & Horn, 1980, Nuc. Acids Res. 9(10): 2331; Matteucchi & Carruthers, 1980, Tetrahedron Letters 21: 719; and Chow and Kempe, 1981, Nuc. Acids Res. 9(12); 2807–2817.

Alternatively, the protein itself could be produced using chemical methods to synthesize the amino acid sequence depicted in FIG. 2A–FIG. 2D in whole or in part. For example, peptides can be synthesized by solid phase techniques, cleaved from the resin and purified by preparative high performance liquid chromatography. (e.g., see, Creighton, 1983, Proteins, Structures and Molecular Principles, W. H. Freeman & Co., N.Y. pp. 50–60). The composition of the synthetic peptides may be confirmed by amino acid analysis or sequencing (e.g., the Edman degradation procedure; see Creighton, 1983, Proteins, Structures and Molecular Principles, W. H. Freeman & Co., N.Y., pp. 34–49).

Human α-GalNAc is a homodimeric glycoprotein. The full-length α-GalNAc cDNA predicts a mature subunit of 394 amino acids. Homology searches with computerized data bases identified short regions of α-GalNAc homology with the yeast Mel 1 and the *E. coli* Mel A amino acid sequences (see FIG. 4A–FIG. 4C; [SEQ ID NOS: 4–7]). It is likely that these conserved regions are important for enzyme conformation, stability, subunit association and/or catalysis. Thus, it is preferred not to alter such conserved regions. However, certain modifications in the coding sequence may be advantageous. For example, the six N-linked glycosylation consensus sequences could be selectively obliterated, thereby altering the glycosylation of the enzyme and affecting phosphorylation, sialylation, sulfation, etc. Such modified enzymes may have altered clearance properties and targeting when injected into patients. Oligosaccharide modifications may be useful in the targeting of α-GalNAc for effective enzyme therapy.

Also, the 5′ untranslated and coding regions of the nucleotide sequence could be altered to improve the translational efficiency of the α-GalNAc mRNA. For example, substitution of a cytosine for the guanosine in position +4 of the α-GalNAc cDNA could improve the translational efficiency of the α-GalNAc mRNA 5- to 10-fold (Kozak, 1987, J. Mol. Biol. 196: 947–950).

In addition, based on X-ray crystallographic data, sequence alterations could be undertaken to improve protein stability, i.e., introducing disulfide bridges at the appropriate positions, and/or deleting or replacing amino acids that are predicted to cause protein instability. These are only examples of enzyme modifications that can be engineered to produce a more active or stable protein, more enzyme protein, or even change the catalytic specificity of the enzyme.

5.2. EXPRESSION OF α-GalNAc

In order to express a biologically active α-GalNAc, the coding sequence for the enzyme, a functional equivalent, or a modified sequence, as described in Section 5.1., supra, is inserted into an appropriate eukaryotic expression vector, i.e., a vector which contains the necessary elements for transcription and translation of the inserted coding sequence in appropriate eukaryotic host cells which posses the cellular machinery and elements for the proper processing, i.e., signal cleavage, glycosylation, phosphorylation and protein sorting. Mammalian host cell expression systems are preferred for the expression of biologically active enzymes that are properly folded and processed; when administered in humans such expression products should exhibit proper tissue targeting and no immunological reaction.

5.2.1. CONSTRUCTION OF EXPRESSION VECTORS AND PREPARATION OF TRANSFECTANTS

Methods which are well-known to those skilled in the art can be used to construct expression vectors containing the α-GalNAc coding sequence and appropriate transcriptional/translational control signals. These methods include in vitro recombination/genetic recombination. See, for example, the techniques described in Maniatis et al., 1982, Molecular Cloning A Laboratory Manual, Cold spring Harbor Laboratory, N.Y., Chapter 12.

A variety of eukaryotic host-expression systems may be utilized to express the α-GalNAc coding sequence. Although prokaryotic systems offer the distinct advantage of ease of manipulation and low cost of scale-up, their major drawback in the expression of α-GalNAc is their lack of proper post-translational modifications of expressed mammalian proteins. Eukaryotic systems, and preferably mammalian expression systems, allow for proper modification to occur. Eukaryotic cells which possess the cellular machinery for proper processing of the primary transcript, glycosylation, phosphorylation, and, advantageously secretion of the gene product should be used as host cells for the expression of α-GalNAc. Mammalian cell lines are preferred. Such host cell lines may include but are not limited to CHO, VERO, BHK, HeLa, COS, MDCK, 293, WI38, etc.

Appropriate eukaryotic vectors should be utilized to direct the expression of the α-GalNAc in the host cell chosen. For example, at least two basic approaches may be followed for the design of such vectors based on SV40. The first is to replace the SV40 early region with the gene of interest while the second is to replace the late region (Hammarskjold, et al., 1986, Gene 43: 41). Early and late region replacement vectors can also be complemented in vitro by the appropriate SV40 mutant lacking the early or late region. Such complementation will produce recombinants which are packaged into infectious capsids and which contain the gene of interest. A permissive cell line can then be infected and produce the recombinant protein. SV40-based vectors can also be used in transient expression studies, where best results are obtained when they are introduced into COS (CV-1, origin of SV40) cells, a derivative of CV-1 (green monkey kidney cells) which contain a single copy of an origin defective SV40 genome integrated into the chromosome. These cells actively synthesize large T antigen (SV40), thus initiating replication from any plasmid containing an SV40 origin of replication.

In addition to SV40, almost every molecularly cloned virus or retrovirus may be used as a cloning or expression vehicle. Viral vectors based on a number of retroviruses (avian and murine), adenoviruses, vaccinia virus (Cochran, et al., 1985, Proc. Natl. Acad. Sci. USA 82: 19) and polyoma virus may be used for expression. Other cloned viruses, such as JC (Howley, et al., 1980, J. Virol 36: 878), BK and the human papilloma viruses (Heilman, et al., 1980, J. Virol 36: 395), offer the potential of being used as eukaryotic expression vectors. For example, when using adenovirus expression vectors the α-GalNAc coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the human enzyme in infected hosts (e.g., see Logan & Shenk, 1984, Proc. Natl. Acad. Sci. (USA) 81: 3655–3659). Alternatively, the vaccinia virus 7.5K promoter may be used (e.g., see, Mackett et al., 1982, Proc. Natl. Acad. Sci. (USA) 79: 7415–7419; Mackett et al., 1984, J. Virol. 49: 857–864; Panicali et al., 1982, Proc. Natl. Acad. Sci. 79: 4927–4931). Of particular interest are vectors based on bovine papilloma virus (Sarver, et al., 1981, Mol. Cell. Biol. 1: 486). These vectors have the ability to replicate as extrachromosomal elements. Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neogene. High level expression may also be achieved using inducible promoters such as the metallothionine IIA promoter, heat shock promoters, etc.

For long-term, high-yield production of recombinant proteins, stable expression is preferred. For example, following the introduction of foreign DNA, engineered cells may be allowed to grow for 1–2 days in an enriched media, and then are switched to a selective media. Rather than using expression vectors which contain viral origins of replication, host cells can be transformed with the α-GalNAc DNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. A number of selection systems may be used, including but not limited to the herpes simplex virus thymidine kinase (Wigler, et al., 1977, Cell 11: 223), hypoxanthine-guanine phosphoribosyltransferase (Szybalska & Szybalski, 1962, Proc. Natl. Acad. Sci. USA 48: 2026), and adenine phosphoribosyltransferase (Lowy, et al., 1980, Cell 22: 817) genes can be employed in $tk^-$, $hgprt^-$ or $aprt^-$ cells, respectively. Also, antimetabolite resistance can be used as the basis of selection for dhfr, which confers resistance to methotrexate (Wigler, et al., 1980, Natl. Acad. Sci. USA 77: 3567; O'Hare, et al., 1981, Proc. Natl. Acad. Sci. USA 78: 1527); gpt, which confers resistance to mycophenolic acid (Mulligan & Berg, 1981, Proc. Natl. Acad. Sci. USA 78: 2072); neo, which confers resistance to the aminoglycoside G-418 (Colberre-Garapin, et al., 1981, J. Mol. Biol. 150: 1); and hygro, which confers resistance to hygromycin (Santerre, et al., 1984, Gene 30: 147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85: 8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

Alternative eukaryotic expression systems which may be used to express the α-GalNAc enzymes are yeast transformed with recombinant yeast expression vectors containing the α-GalNAc coding sequence; insect cell systems infected with recombinant virus expression vectors (e.g., baculovirus) containing the α-GalNAc coding sequence; or plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the α-GalNAc coding sequence.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 31987, Acad. Press, N.Y., Vol. 153, pp.516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II. For complementation assays in yeast, cDNAs for α-GalNAc may be cloned into yeast episomal plasmids (YEp)

which replicate autonomously in yeast due to the presence of the yeast 2μ circle. The cDNA may be cloned behind either a constitutive yeast promoter such as ADH or LEU2 or an inducible promoter such as GAL (Cloning in Yeast, Chpt. 3, R. Rothstein In: DNA Cloning Vol.11, A Practical Approach, Ed. DM Glover, 1986, IRL Press, Wash., D.C.). Constructs may contain the 5' and 3' non-translated regions of the cognate α-GalNAc mRNA or those corresponding to a yeast gene. YEp plasmids transform at high efficiency and the plasmids are extremely stable. Alternatively, vectors may be used which promote integration of foreign DNA sequences into the yeast chromosome.

In cases where plant expression vectors are used, the expression of the α-GalNAc coding sequence may be driven by any of a number of promoters. For example, viral promoters such as the 35S RNA and 19S RNA promoters of CaMV (Brisson et al., 1984, Nature 310: 511–514), or the coat protein promoter of TMV (Takamatsu et al., 1987, EMBO J. 6: 307–311) may be used; alternatively, plant promoters such as the small subunit of RUBISCO (Coruzzi et al., 1984, EMBO J. 3: 1671–1680; Broglie et al., 1984, Science 224: 838–843); or heat shock promoters, e.g., soybean hsp17.5-E or hsp17.3-B (Gurley et al., 1986, Mol. Cell. Biol. 6: 559–565) may be used. These constructs can be introduced into plant cells using Ti plasmids, Ri plasmids, plant virus vectors; direct DNA transformation; microinjection, electroporation, etc. For reviews of such techniques see, for example, Weissbach & Weissbach, 1988, Methods for Plant Molecular Biology, Academic Press, N.Y., Section VIII, pp. 421–463; and Grierson & Corey, 1988, Plant Molecular Biology, 2d Ed., Blackie, London, Ch. 7–9.

An alternative expression system which could be used to express α-GalNAc is an insect system. In one such system, *Autographa californica* nuclear polyhedrosis virus (AcNPV) is used as a vector to express foreign genes. The virus grows in *Spodoptera frugiperda* cells. The α-GalNAc coding sequence may be cloned into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., see Smith et al., 1983, J. Viol. 46: 584; Smith, U.S. Pat. No. 4,215,051).

5.2.2. IDENTIFICATION OF TRANSFECTANTS OR TRANSFORMANTS EXPRESSING THE α-GalNAc GENE PRODUCT

The host cells which contain the α-GalNAc coding sequence and which express the biologically active gene product may be identified by at least four general approaches: (a) DNA-DNA or DNA-RNA hybridization; (b) the presence or absence of "marker" gene functions; (c) assessing the level of transcription as measured by the expression of α-GalNAc mRNA transcripts in the host cell: and (d) detection of the gene product as measured by immunoassay or by its biological activity.

In the first approach, the presence of the α-GalNAc coding sequence inserted in the expression vector can be detected by DNA-DNA or DNA-RNA hybridization using probes comprising nucleotide sequences that are homologous to the α-GalNac coding sequence substantially as shown in FIG. 2A–FIG. 2D, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the α-GalNAc coding sequence is inserted within a marker gene sequence of the vector, recombinants containing the α-GalNAc coding sequence can be identified by the absence of the marker gene function. Alternatively, a marker gene can be placed in tandem with the α-GalNAc sequence under the control of the same or different promoter used to control the expression of the α-GalNAc coding sequence. Expression of the marker in response to induction or selection indicates expression of the α-GalNAc coding sequence.

In the third approach, transcriptional activity for the α-GalNAc coding region can be assessed by hybridization assays. For example, RNA can be isolated and analyzed by Northern blot using a probe homologous to the α-GalNAc coding sequence or particular portions thereof substantially as shown in FIG. 2A–FIG. 2D. Alternatively, total nucleic acids of the host cell may be extracted and assayed for hybridization to such probes.

In the fourth approach, the expression of the α-GalNAc protein product can be assessed immunologically, for example by Western blots, immunoassays such as radioimmuno-precipitation, enzyme-linked immunoassays and the like. The ultimate test of the success of the expression system, however, involves the detection of the biologically active α-GalNAc gene product. Where the host cell secretes the gene product, the cell free media obtained from the cultured transfectant host cell may be assayed for α-GalNAc activity. Where the gene product is not secreted, cell lysates may be assayed for such activity. In either case, a number of assays can be used to detect α-GalNAc activity including but not limited to: (a) activity toward 4-methylumbelliferyl-α-N-acetylgalactosaminylpyranoside as described by Sweda et al., 1989, Can. J. Chem. 67: 1388–1391, and applied by Schindler, et al., 1989, N. Engl. J. Med. 320: 1735–1740; and/or (b) activity toward p-nitrophenyl-α-N-acetylgalactosaminylpyranoside (Van Diggelen, et al., 1988, J. Inherit. Metab. Dis. 11: 349–357); and the like.

5.2.3. PURIFICATION AND CHARACTERIZATION OF THE α-GalNAc GENE PRODUCT

Once a clone that produces high levels of biologically active α-GalNAc is identified, the clone may be expanded and used to produce large amounts of the enzyme which may be purified using techniques well-known in the art including, but not limited to immunoaffinity purification, chromatographic methods including high performance liquid chromatography and the like. Where the enzyme is secreted by the cultured cells, α-GalNAc may be readily recovered from the culture medium.

Where the α-GalNAc coding sequence is engineered to encode a cleavable fusion protein, the purification of α-GalNAc may be readily accomplished using affinity purification techniques. For example, a collagenase cleavage recognition consensus sequence may be engineered between the carboxy terminus of α-GalNAc and protein A. The resulting fusion protein may be readily purified using an IgG column that binds the protein A moiety. Unfused α-GalNAc may be readily released from the column by treatment with collagenase. In this aspect of the invention, any cleavage site or enzyme cleavage substrate may be engineered between the α-GalNAc sequence and a second peptide or protein that has a binding partner which could be used for purification, e.g., any antigen for which an immunoaffinity column can be prepared.

5.2.4. MODIFIED GLYCOFORMS OF RECOMBINANT α-GalNAc

Modifications of the recombinant α-GalNAc may be desired for a variety of reasons; e.g., altered tissue targeting in vivo, altered biological activity, etc. In particular, the invention includes selective deglycosylation of the complex high mannose carbohydrate moieties covalently attached to the recombinant enzyme to produce various glycoforms of recombinant α-GalNAc. Such modifications include but are not limited to sequential deglycosylation by neuraminidase to expose terminal galactose, β-galactose; β-galactosidase treatment to expose N-β-acetylglucosaminyl residues; and N-β-acetylglucosaminidase treatment to expose mannose residues.

Deglycosylation of recombinant α-GalNAc may be accomplished in a number of ways. The general methods of sequential treatment by exo-glycosidases are essentially those previously described (Murray, 1987, Meth. Enzymol. 149: 25). Briefly, terminal sialic acid residues may be removed by treatment with neuraminidase covalently bound to agarose. To this end, type VI neuraminidase (SIGMA Chemical Co., St. Louis, Mo.) attached to agarose at 40 U/g may be used to treat α-GalNAc; e.g., 100 mg α-GalNAc may be treated with 8 units of neuraminidase conjugate at pH 5.0 for 4 hours at 37° C. The conjugated neuramindase can be removed by centrifugation. Similarly, β-galactosidase (3 Units per 100 mg α-GalNAc) purified from *Streptococcus pneumoniae* may be used to remove terminal galactose residues. Finally, jack bean N-β-acetylglucosaminidase (SIGMA Chemical Co., St. Louis, Mo.) can be utilized; e.g., $3\times10^6$ units mixed with each 100 mg aliquot of recombinant α-GalNAc at 37° C. for four hours. At each step, the recombinant enzyme can be rapidly purified free of deglycosylating enzyme and free carbohydrate by purification of α-GalNAc as previously described (Schindler, et al., 1989, N. Eng. J. Med. 320: 1735–1740).

5.3. USES OF THE RECOMBINANT α-GalNAc

The purified products obtained in accordance with the invention may be advantageously utilized for enzyme replacement therapy in patient with the lysosomal storage disorder, Schindler's disease (α-GalNAc). Schindler disease is a recently identified inborn error of glyconjugate metabolism in which the deficient activity of α-GalNAc results in the accumulation of glycoconjugates. The type I disease has been characterized as a neuroaxonal dystrophy and the type II disease has a milder phenotype characterized by angiokeratoma and a minimal to moderate mental retardation (Schindler, et al., 1989, N. Engl. J. Med. 320: 1735–1740; Kanzaki, et al., 1989, Lancet 1: 875–877).

The purified product of active α-GalNAc may also be used for the hydrolyses of α-N-acetylgalactosaminyl and mannosyl residues of various glycoconjugates, including but not limited to the blood group A substance on erythrocytes, other glycolipids, glycoproteins and glycopeptides.

6. EXAMPLE: CLONING AND EXPRESSION OF BIOLOGICALLY ACTIVE α-GALNAC

The subsections below describe the production of active human recombinant α-Galactosidase B (α-GalNAc). To isolate a full-length cDNA, the enzyme from human lung was purified to homogeneity, 129 non-overlapping amino acids were determined by microsequencing the N-terminus and seven tryptic peptides, and four synthetic oligonucleotide mixtures were used to screen a human fibroblast cDNA library. A full-length cDNA, pAGB-3, isolated from a placental λgt11 cDNA library, had a 2158 bp insert with an open reading frame which predicted an amino acid sequence that was colinear with all 129 microsequenced residues of the purified enzyme. The pAGB-3 insert had a 344 bp 5′ untranslated region, a 1236 bp open reading frame encoding 411 amino acids, a 514 bp 3′ untranslated region, and a 64 bp poly(A) tract. A signal peptide sequence of 17 amino acids as well as six N-glycosylation sites were predicted. The pAGB-3 cDNA was subcloned into the p91023(B) mammalian expression vector and human α-GalNAc activity was transiently expressed in COS-1 cells, demonstrating the functional integrity of the full-length cDNA. Northern hybridization analysis of mRNA revealed two transcripts of about 3.6 and 2.2 kb, and primer extension studies indicated a cap site at nt −347 for the 2.2 kb cDNA. Isolation of a genomic clone, gAGB-1, and sequencing the 2048 bp region including pAGB-3 revealed a 1754 bp intron between codons 319 and 320, which also was the site of a 70 bp insertion (Tsuji, et al., 1990, Biochim. Biophys. Res. Commun. 163: 1498–1504) and a 45 bp deletion in other cDNA clones. Notably, the α-GalNAc cDNA had remarkable amino acid homology with human α-Gal A cDNA, suggesting the evolutionary relatedness of these genes. The α-GalNAc cDNA had 46.9% to 64.7% amino acid idenity in sequences (codons 1–319) corresponding to α-Gal A exons 1 through 6, while the comparable exon 7 sequence (pAGB-3 codons 320–411) had only 15.8% homology with numerous gaps. These findings implicate the genomic region at and surrounding codon 319 as a potential site for the abnormal processing of α-GalNAc transcripts as well as for a recombinational event in the evolution and divergence of α-Gal A and α-GalNAc. The availability of the full-length cDNA for human α-GalNAc will permit studies of the genomic organization and evolution of this lysosomal gene, as well as the characterization of the molecular lesions causing Schindler disease.

6.1. MATERIALS AND METHODS

6.1.1. AFFINITY PURIFICATION, MICROSEQUENCING AND ANTIBODY PRODUCTION

Human lung α-GalNAc was purified to homogeneity, polyclonal rabbit anti-human α-GalNAc antibodies were produced and purified, and cell supernatants were immunoblotted as described previously (Schindler, et al., 1989, N. Engl. J. Med. 320: 1735–1740; Bishop & Desnick, 1981, J. Biol. Chem. 256: 1307–1316; Calhoun, et al., 1985, Proc. Natl. Acad. Sci. USA 82: 7364–7368). For the isolation of tryptic peptides, the concentrated post-hydroxylapatite fraction was subjected to preparative 10% $NaDodSO_4$/PAGE and the 48 and 117 kDa α-GalNAc species were electroeluted separately (Hunkapillar, et al., 1973, Methods Enzymol. 91: 227–236), digested with tosylphenylalaninechloromethylketone-treated trypsin, and the resulting tryptic peptides from each species were separated by C8 reversed-phase HPLC (Tsai, et al., 1988, Proc. Natl. Acad. Sci. USA 55: 7049–7053). The N-terminal amino acid sequences of both the 48 and 117 kDa species and the sequences of selected tryptic peptides from the 48 kDa species were determined by automated gas-phase micro-sequencing and HPLC identification of phenylthiohydantoin amino acid derivatives (Hunkapillar & Hood, 1983, Science 219: 650–654, 659).

6.1.2. CONSTRUCTION OF SYNTHETIC OLIGONUCLEOTIDE PROBES

Mixed and unique oligonucleotides were synthesized on an Applied Biosystems Model 380B oligonucleotide synthesizer. Four oligonucleotide mixtures were constructed to regions of minimal codon redundancy for the following N-terminal and tryptic peptide sequences: N-terminus [5'-CA(AG)ACNCCNCCNATGGG-3'][SEQ ID NO: 12]; peptide T-106A [AA(TC)AT(T-CA)GA(TC)GA(TC)TG(TC)TGGAT(T-CA)GGNGG-3'][SEQ ID NO: 13]; peptide T-72 [5'-ACNTT(TC)GCNGA(AG)TGGAA-3'][SEQ ID NO: 14]; and peptide T-133, [5'-TGGCCNGCNTA(TC-)GA(AG)GG-3'][SEQ ID NO: 15]. Oligonucleotide probes for library screening were 5' end-labelled with [γ-$^{32}$P]ATP using T4 polynucleotide kinase (Maniatis, et al., 1982, Molecular Cloning: A Laboratory Manual, pp. 309–328, Cold Spring Harbor Laboratories, NY, N.Y.). Unique sequence oligonucleotides (17-mers) were synthesized and used as primers in sequencing reactions. To determine the cap site, two unique, overlapping 30-mers were synthesized for primer extension, 5'-TCGGGACTCCCAGCACTGCAGAGGGTGT-GA-3'[SEQ ID NO: 16] and 5'-CTGCAGAGGGTGTGAGGTCTGACATC-CAGG-3'[SEQ ID NO: 17]. To detect alternatively spliced transcripts, PCR sense and antisense primers for the exonic region flanking the putative 70 bp insertion had the sequences 5'-AGTCGAATTCTGATGT-CCACAGACCTGCGT-3'[SEQ ID NO: 18], and 5'-AGTCGTCGAGCATATCGGTCCTGCAGCTGA-3'[SEQ ID NO: 19], respectively. The four PCR primer sequences for the construction of the α-Gal A and α-GalNAc hybrid cDNA were α-Gal A sense, 5'-TGGGGAGTAGATCTGCTAAAA-3'[SEQ ID NO: 20]; α-Gal antisense, 5'-GAT-GAGAGATTTTTCCTGTCTAAGCTGGTACCC-3'[SEQ ID NO: 21]; α-GalNAc sense, 5'-TACCAGCT-TAGACAGGAAAAATCTCTCATCGAA-3'[SEQ ID NO: 22]; and α-GalNAc antisense, 5'-AAGAGGT-CAGATCTCTCTACT-3'[SEQ ID NO: 23].

6.1.3. ISOLATION AND CHARACTERIZATION OF cDNA AND GENOMIC CLONES

The pcD human fibroblast cDNA library, kindly provided by Dr. Hiroto Okayama (NIH), was screened with the radiolabelled 26-mer oligonucleotide mixture corresponding to tryptic peptide T-106A by colony hybridization (Tsai, et al., 1988, Proc. Natl. Acad. Sci. USA 55: 7049–7053). Plasmid DNA isolation and Southern hybridization analyses of positive clones were performed as previously described (Maniatis, et al., 1982, Molecular Cloning: A Laboratory Manual, pp. 309–328, Cold Spring Harbor Laboratories, NY, N.Y.). For isolation of a full-length cDNA, a 0.9 kb BamHI fragment corresponding to the 5' portion of the pAGB-1 insert was then isolated, nick-translated, and used to screen recombinants from a λgt11 human placental library (Clontech Laboratories, Palo Alto, Calif.) by plaque hybridization (Maniatis, et al., 1982, Molecular Cloning: A Laboratory Manual, pp. 309–328, Cold Spring Harbor Laboratories, NY, N.Y.). To isolate genomic clones containing the entire α-GalNAc sequence, $1\times10^6$ recombinants from a human genomic cosmid library were screened with the radiolabelled pAGB-3 cDNA insert using the conditions described above for cDNA library screening. The genomic library was prepared from size-selected human lymphoblast DNA and kindly was provided by Dr. Henrik Vissing (Mount Sinai School of Medicine).

6.1.4. DNA SEQUENCING AND COMPUTER-ASSISTED ANALYSES

The BamHI inserts from pAGB-1 and a EcoRI-BamHI restriction fragment of pAGB-3 were subcloned into M13 mp18 and mp19. All DNA sequencing reactions were carried out by primer extension using either M13 universal primers or α-GalNAc-specific oligonucleotide primers by the dideoxy method in both orientations (Sanger, et al., 1980, J. Mol. Biol. 143: 161–178). Searches for nucleotide and amino acid sequence similarity were carried out with the University of Wisconsin Genetics Computer Group Software (Wolf, et al., 1988, CABIOS. 4: 187–191). Computer-assisted RNA folding was performed with the PCFOLD program (Zuker, 1989, Methods Enzymol. 180: 262–288).

6.1.5. TRANSIENT EXPRESSION ASSAYS

The human α-GalNAc full-length pAGB-3 cDNA insert was subcloned into the p91023(B) eukaryotic expression vector (Wong, et al., 1985, Science 228: 810–813), kindly provided by Dr. R. J. Kaufmann (Genetics Institute, Boston, Mass.). Plasmid DNA from the construct (designated p91-AGB-3) was purified and COS-1 monkey kidney cells were transfected with 10 μg of the p91-AGB-3 plasmid DNA by calcium-phosphate precipitation (Chen & Okayama, 1987, Mol. Cell. Biol. 7: 2745–2752). Cells were harvested at 24 hour intervals after transfection and assayed for α-GalNAc activity as previously described (Schindler, et al., 1989, N. Engl. J. Med. 320: 1735–1740). One unit (U) of enzymatic activity is equal to that amount of enzyme required to hydrolyze 1 nmol of 4-MU-α-GalNAc per hour. Protein concentrations were determined by the fluorescamine method (Bishop & Desnick, 1981, J. Biol. Chem. 256: 1307–1316).

6.1.6. NORTHERN HYBRIDIZATION AND CAP SITE ANALYSES

Total RNA was isolated from human lymphoblasts, fibroblasts, and placentae and northern hybridization was performed using the nick-translated pAGB-3 insert as probe (Maniatis, et al., 1982, Molecular Cloning: A Laboratory Manual, pp. 309–328, Cold Spring Harbor Laboratories, NY, N.Y.). Alternatively, the pAGB-3 insert was subcloned into pGEM-4Z (Promega, Madison, Wis.) and radiolabelled α-GalNAc riboprobe, rbAGB-3, was generated using the Promega riboprobe system and used for northern hybridization. For identification of the α-GalNAc cap-site, two unique, overlapping 30-mer oligonucleotide primers were synthesized corresponding to regions 60 and 75 bp from the 5' end of the pAGB-3 cDNA and end-labelled (Maniatis, et al., 1982, Molecular Cloning: A Laboratory Manual, pp. 309-328, Cold Spring Harbor Laboratories, NY, N.Y.). Each primer (100 ng) was used to extend 10 μg of total placental RNA with the BRL cDNA Synthesis Kit (BRL, Gaithersburg, Md.). First-strand synthesis was terminated by phenol extraction and ethanol precipitation. The pellet was washed three times with 70% ethanol, resuspended in 6 μl of $H_2O$, and then mixed with 6 μl of loading dye (0.3% xylene cyanol, 0.3% bromophenol blue, 0.37% EDTA, pH 7.0). The RNA/DNA heteroduplexes were denatured at 65° C. for 3 minutes and an aliquot was electrophoresed on a standard 8M urea, 8% polyacrylamide sequencing gel.

6.1.7. CONSTRUCTION OF p91-α-GalA6/α-GalNAc7

A plasmid containing α-Gal A exons 1 through 6 from pcDAG-126 (Bishop, et al., 1988, Proc. Natl. Acad. Sci. USA 85: 3903-3907) was ligated to the 3' region of pAGB-3 α-GalNAc insert which corresponded in position to α-Gal A exon 7. The hybrid cDNA, designated α-GalA6/α-GalNAc7 was constructed with the sense and antisense primers indicated above using a PCR-based method (Ho, et al., 1989, Gene 77: 51-59) and sequenced. The α-GalA6/α-GalNAc7 insert was subcloned into the expression vector, p91023(B), and the construct was transiently expressed in COS-1 cells as described above. The α-Gal A and α-GalNAc enzymatic activities and enzyme proteins were detected with 4-MU substrates and by immunoblotting with the respective polyclonal antibodies as described above.

6.1.8. PRIMER EXTENSION AND PCR AMPLIFICATION OF cDNA AND GENOMIC SEQUENCES

For PCR amplification of the putative alternatively spliced region, the 30-mer sense and antisense primers (described above) were used to amplify the (a) reverse-transcribed mRNA from various human sources; (b) cDNA inserts from clones pAGB-4 to 34; and (c) the gAGB-1 genomic sequence. DNAs from pAGB-4 to 34 cDNA clones and the gAGB-1 genomic clone were isolated as described (Tsai, et al., 1988, Proc. Natl. Acad. Sci. USA 55: 7049-7053; and, Maniatis, et al., 1982, Molecular Cloning: A Laboratory Manual, pp. 309-328, Cold Spring Harbor Laboratories, NY, N.Y.). cDNA was synthesized from 10 μg of lymphoblast, fibroblast, and placental total RNA or 2.5 μg of brain Poly(A)+ mRNA (Clontech, Palo Alto, Calif.) using the BRL cDNA Synthesis Kit. Bacteriophage DNA (~0.1 μg) and reverse-transcribed mRNA (~0.1 μg) or genomic cosmid DNA (~1 μg) was PCR-amplified using 20 μM of each primer and the GeneAmp DNA Amplification Reagent Kit (Perkin Elmer Cetus, Norwalk, Conn.). Each PCR cycle consisted of 1 minute denaturation at 94° C.; 2 minute annealing at 37° C.; and a 7 minute extension at 60° C. The PCR products were phenol extracted, ethanol precipitated and resuspended in 20 μl of $H_2O$. An aliquot (2 μl) of each PCR reaction was analyzed by electrophoresis on agarose gels using HindIII digested lambda and HaeIII digested ΦX174 DNAs as size standards. For identification of potential stops during reverse transcription of the region surrounding the pcD-HS1204 insertion, a unique 32-mer, 5'-AGTAGTAAGCTTTCATATAT-CACAGACCCGGT-3'[SEQ ID NO: 24], was used to extend 10 μg of total placental RNA or 1 μg of rbAGB-3 generated in vitro by the Promega riboprobe system as described above.

6.2. RESULTS

6.2.1. PURIFICATION AND CHARACTERIZATION OF HUMAN α-GalNAc

Human α-GalNAc was purified to homogeneity (specific activity=~370,000 U/mg protein) as assessed by the presence of only the 48 and 117 kDa species on $NaDodSO_4$/PAGE (FIG. 1C). The 117 kDa species was not reduced by boiling or by dialysis against 8M urea in the presence of β-mercaptoethanol. The 27 microsequenced N-terminal residues of the electroeluted 117 kDa species were identical to those of the 48 kDa species. Further evidence that the 117 kDa species was a homodimer of the 48 kDa glycoprotein subunit was the finding that the tryptic digests (and chymotryptic digests) of both species had essentially identical HPLC profiles (FIG. 1A–FIG. 1B). Microsequencing of the N-terminus and seven tryptic peptides from the 48 kDa species identified a total of 129 non-overlapping α-GalNAc residues. For library screenings, synthetic oligonucleotide mixtures (17- to 26-mers) were constructed to contain all possible codons for selected amino acid sequences from the N-terminus and three internal tryptic peptides (FIGS. 1A, B and 2).

6.2.2. ISOLATION, CHARACTERIZATION AND EXPRESSION OF A FULL-LENGTH cDNA

Screening of $2 \times 10^6$ recombinants from the pcD human fibroblast cDNA library with a 26-mer oligonucleotide mixture of 576 species corresponding to internal peptide T-106A detected two putative positive clones. pAGB-1, which hybridized with all four oligonucleotide mixtures, had a 1.8 kb insert with an open reading frame of 1242 bp, a 514 bp 3' untranslated region, and a poly(A) tract, but no apparent 5' untranslated sequence. Authenticity was established by colinearity of the pAGB-1 insert's predicted amino acid sequence with 129 microsequenced residues of the purified protein. In order to isolate a full-length cDNA, the 0.9 kb 5' BamHI fragment from the pAGB-1 insert was radiolabelled and used to screen a human placental cDNA library. Of 32 putative positive clones (pAGB-3 to 34), pAGB-3 contained the longest insert and was sequenced in both orientations. As shown in FIG. 2A–FIG. 2D, the 2158 bp pAGB-3 insert had a 344 bp 5' untranslated region, a 1236 bp open reading frame which encoded 411 amino acids, a 514 bp 3' untranslated region and a 64 bp poly(A) tract. An upstream, inframe ATG occurred at −192 nt, but there were inframe termination codons at −141, −135, and −120 nt, indicating that the −192 ATG was non-functional. A single consensus polyadenylation signal (AATAAA) and a consensus recognition sequence (CACTG) for the U4 small nuclear ribonucleoprotein (Berget, 1984, Nature (London) 309: 179-182) were located 16 and 65 bp from the poly(A) tract, respectively. In retrospect, the partial cDNA, pAGB-1 had the entire 1236 bp coding region as well as 6 bp of 5' untranslated sequence.

Analysis of the deduced amino acid sequence of pAGB-3 indicated a signal peptide sequence of 17 residues since Leu-18 was the N-terminal residue of the micro-sequenced mature enzyme. When the weight matrix method of von Heijne (von Heijne, 1986, Nucleic Acids Res. 14: 4683- 4960) was used to predict the peptidase cleavage site, the preferred site, between Ala-13 and Gln-14, had a score of 4.34, whereas cleavage after Met-17 had a score of 2.38. The predicted molecular mass of the 394 residue mature, unglycosylated enzyme subunit ($M_r$=44,700) was consistent with that (48 kDa) estimated by $NaDodSO_4$/PAGE of the purified glycosylated enzyme. These findings suggest that the mature glycoprotein subunit had at least two N-linked oligosaccharide chains, although there were six putative N-glycosylation sites at Asn residues 124, 177, 201, 359, 385 and 391 (FIG. 2A–FIG. 2D).

For transient expression, the pAGB-3 full-length cDNA insert was subcloned into the eukaryotic expression vector p91023(b) and the construct, p91-AGB-3, was transfected into COS-1 monkey kidney cells. Compared to the endogenous mean α-GalNAc activity in mock transfected COS-1 cells (35 U/mg; range: 23–50 U/mg; n=6), the transfected cells had a mean activity of 600 U/mg (range: 104–2,400 U/mg; n=6) 72 hours after transfection, or about 17 times the endogenous activity. The expressed human enzyme protein also was detected by immunoblot analysis using rabbit-anti-human α-GalNAc antibodies, whereas the endogenous monkey enzyme was variably visible as a faint band at ~40 kDa or was not detectable (FIG. 3). The expressed human enzyme subunit had a moleular weight of ~48 kDa, indicating that it was glycosylated.

6.2.3. NORTHERN HYBRIDIZATION AND CAP-SITE ANALYSES

Northern hybridization analyses revealed two transcripts in total, cytoplasmic, or poly(A)+ RNA of about 2.2 and 3.6 kb, which were present in similar amounts. The cap-site was determined to be at −347, or 3 nt beyond the 5′ end of the pAGB-3 cDNA insert by primer extension of total placental RNA using two overlapping oligonucleotide probes. The 3.6 kb transcript was the result of a downstream polyadenylation signal.

6.2.4. SEQUENCE HOMOLOGY BETWEEN α-GalNAc WITH α-Gal A

Computer-assisted searches of nucleic acid and protein data bases revealed no significant amino acid sequence similarities between α-GalNAc and that of any other DNA or protein sequence except for human α-Gal A (Bishop, et al., 1988, Proc. Natl. Acad. Sci. USA 85: 3903–3907). Comparison of the nucleic acid and deduced amino acid sequences of the full-length α-GalNAc and α-Gal A cDNAs revealed 55.8% and 46.9% overall homology, respectively. Since the intron-/exon junctions and the entire genomic sequence encoding human α-Gal A have been determined (Bishop, et al., 1988, Proc. Natl. Acad. Sci. USA 85: 3903–3907; and, Kornreich, et al., 1989, Nucleic Acids Res. 17: 3301–3302), it was possible to compare the α-GalNAc amino acid sequence with those deduced from each of the seven α-Gal A exons (FIG. 4A–FIG. 4C). Notably, there was remarkable identity (56.4%) between the α-GalNAc sequences corresponding to those of α-Gal A exons 1 through 6. For example, all eight cysteine residues in α-GalNAc were present in the identical positions in α-Gal A. Of the 14 proline and 23 glycine residues in α-Gal A, 10 and 20 were conserved in identical positions in α-GalNAc, respectively. Furthermore, all four of the α-Gal A N-glycosylation sites were conserved in α-Gal B. Putative functional domains were suggested by shorter stretches of amino acid homology shared by α-GalNAc, α-Gal A, yeast α-galactosidase (Mel 1) (Liljestrom, 1985, Nucleic Acids Res. 13: 7257–7268) and/or *E. coli* α-galactosidase (Mel A) (Liljestrom and Lijestrom, 1987, Nucleic Acids Res. 15: 2213–2220) in α-Gal A exons 1 through 6. In contrast, there was little, if any, similarity in the predicted α-GalNAc carboxy-terminal amino acid sequence after residue 319 which corresponded to α-Gal A exon 7 (15.8% homology with numerous gaps). In addition, there were no significant similarities for the cDNAs encoding other human lysosomal polypeptides, with the exception of a short α-GalNAc sequence (residues 365 to 371) in which six out of seven amino acids were identical to residues 194 to 200 in the β-hexosaminidase α-chain, a lysosomal polypeptide with N-acetylgalactosaminidase specificity (Proia, 1988, Proc. Natl. Acad. Sci. USA 85: 1883–1887). These findings suggested that a cDNA construct containing α-Gal A exons 1–6 joined to α-GalNAc exon 7 might express a hybrid protein with a α-Gal A and B activities. Therefore, a hybrid cDNA containing α-Gal A exons 1 through 6 (nt 60–1029) and α-GalNAc exon 7 (nt 958–1258) was constructed and expressed in COS-1 cells; although immunoreactive protein was detected, the protein had no enzymatic activity for either α-Gal A or α-GalNAc.

The finding of extensive homology between α-GalNAc and α-Gal A suggested that they evolved by duplication and divergence of an ancestral sequence for α-Gal A exons 1 through 6. Although there is little, if any, homology among the other lysosomal amino acid sequences (i.e., no "lysosomal domains"), there are notable examples of lysosomal enzyme subunits, pseudogenes or gene families which presumably evolved by duplication and divergence (e.g., Proia, 1988, Proc. Natl. Acad. Sci. USA 85: 1883–1887; Horowitz, et al., 1989, Genomics 4: 87–96; and, Schuchman, et al., 1990, Genomics 6: 149–158). Future comparison of the α-GalNAc and α-Gal A intron/exon boundaries should provide further information on the evolution of these lysosomal genes which encode structurally related, but functionally specific glycohydrolases.

6.2.5. PRIMER EXTENSION AND PCR AND SEQUENCE ANALYSES OF cDNA AND GENOMIC SEQUENCES

During the course of these studies, Tsuji et al. reported a similar human α-GalNAc cDNA sequence (Tsuji, S., et al., 1989, Biochem. Biophys. Res. Comm. 163: 1498–1504) which differed from pAGB-3 by a 70 bp insertion after nt 957 (FIG. 5A; SEQ ID NO: 10) and by several substitutions (nt 493, 494, 524, 614 and 667). The 70 bp insertion consisted of three inverted repeats (nt 919–926, 919–936 and 919–944) and a direct repeat (nt 940–957) from the pAGB-3 coding sequence nt 919 to 957. Analysis of the pAGB-3 cDNA sequence from nt 760–1053 using an RNA folding program (Zuker, 1989, Methods Enzymol. 180: 262–288) predicted a stem and loop structure from nt 918 to 937 (FIG. 5A; SEQ ID NO: 8) which could stall or stop reverse transcription of the α-GalNAc mRNA during cDNA synthesis. To determine if this secondary structure could cause cDNA synthesis errors in library construction, a 32-mer oligonucleotide primer was used to extend total placental RNA and α-GalNAc transcripts generated in vitro with the riboprobe construct, rbAGB-3. Stops of varying intensity were observed from nt 903 to 1009, including two weak stops at the 3′ base (nt 940) and 5′ end (nt 921) of the stem and loop structure (FIG. 5A--FIG. 5D). However, there were no strong stops in this region. Although the actual mechanism is unknown, these findings were consistent with the 70 bp insertion resulting from a complex abnormality involving an RNA-DNA duplex in cDNA library construction (Roberts, et al., 1989, Mol. Cell. Biol. 9: 468–476). Another possibility would be an insertion due to a complex strand-switching event involving DNA polymerase I (Papanicolaou & Ripley, 1989, J. Mol. Biol. 207: 335–353).

Alternatively, this 70 bp insertion may have resulted from alternative splicing, although the insertion predicts a truncated α-GalNAc polypeptide of 358 residues. To investigate the possible occurrence of α-GalNAc transcripts with a 70 bp insertion after pAGB-3 nt 957, PCR was used to amplify this region in (a) reverse-transcribed mRNA from various sources; (b) the cDNA inserts from clones pAGB-4 to 34; and (c) the gAGB-1 genomic clone. If the cDNA inserts or reverse-transcribed RNAs contained the 70 bp insert, a 290 bp PCR product would be observed, whereas the absence of the insert would result in a 220 bp PCR product. Only the 220 bp product was observed in PCR-amplified reverse-transcribed total RNA from human lymphoblasts, fibroblasts, and placenta, or in Poly(A)+ mRNA from brain. Thus, these analyses did not detect longer or shorter transcripts. All of the pAGB-4 through 34 cDNA inserts had only the 220 bp PCR product with the exception of pAGB-13, which had an inframe 45 bp deletion after pAGB-3 nt 957 (i.e., deleted nt 958 to 993). A short direct repeat (ACAAG) was present at both breakpoint junctions. Notably, the deletion occurred at the identical 5′ site of the 70 bp insertion in pcD-HS1204 (Tsuji, et al., 1989, Biochim. Biophys. Res. Commun. 163: 1498–1504; FIG. 5A).

Subsequent sequencing of the region including pAGB-3 codons 254 to 351 in the genomic clone, gAGB-1, revealed a 2048 bp sequence containing a 1754 bp intron between pAGB-3 nt 957 and 958. The intronic sequence had no homology with α-Gal A intron 6, contained two Alu-repetitive sequences in reverse orientation and did not have the 70 bp insertion in either orientation (FIG. 5C–FIG. 5D; SEQ ID NO: 11). It was remarkable that both the pAGB-13 deletion and the pcD-HS1204 insertion occurred at the 5′ donor splice site, nt 957, of this intron. Perhaps the location of the consensus lariat branch point sequences in the intron far upstream (94 and 199 bp) from the 3′ splice site may impair splicing (Reed & Maniatis, 1988, Genes Dev. 2: 1268–1276). This concept is supported by the pAGB-13 deletion in which the more closely positioned cryptic lariat branch point and 3′ splice site were used. Thus, this intron or surrounding region may have a unique sequence and/or secondary structure that impairs the fidelity of hnRNA processing. Since the intron/exon junction after coding nt 957 also is the site of divergence between the α-Gal A and B sequences, this region also may be mechanistically important in the evolution of human α-GalNAc.

7. DEPOSIT OF MICROORGANISMS

The following *E. coli* strains carrying the listed plasmids have been deposited with the Agricultural Research Culture Collection (NRRL), Peoria, Ill. and have been assigned the following accession number:

| Host | Strain | Plasmid | Accession No. |
|---|---|---|---|
| *E. coli* | k12 | pAGB-3 | Pi- 18724 |

The present invention is not to be limited in scope by the microorganisms deposited since the deposited embodiments are intended as illustration of individual aspects of the invention and any microorganisms, or constructs which are functionally equivalent are within the scope of this invention. Indeed various modifications of the invention in addition to those shown and described herein will become apparent to those skilled in the art from the foregoing description and accompanying drawings. Such modifications are intended to fall within the scope of the appended claims.

What is claimed is:

1. A method for producing human α-N-acetylgalactosaminidase comprising:

(a) culturing a eukaryotic cell containing a chromosomally integrated nucleotide sequence encoding human α-N-acetylgalactosaminidase controlled by a regulatory sequence that promotes gene expression and a selectable marker controlled by the same or different regulatory sequence, so that the α-N-acetylgalactosaminidase nucleotide sequence is stably overexpressed and an enzymatically active α-N-acetylgalactosaminidase enzyme is secreted by the eukaryotic cell; and (b) isolating enzymatically active α-N-acetylgalactosaminidase enzyme from the eukaryotic cell culture.

2. The method according to claim 1 wherein, in the presence of selection, the chromosomally integrated nucleotide sequences are amplified.

3. The method according to claim 1 in which the nucleotide sequence encoding the human α-N-acetylgalactosaminidase encodes the amino acid sequence depicted in FIG. 2A to FIG. 2D from amino acid residue 1 to 396.

4. The method according to claim 1 in which the nucleotide sequence encoding the human α-N-acetylgalactosaminidase encodes the amino acid sequence depicted in FIG. 2A to FIG. 2D from amino acid residue 18 to 396.

5. The method according to claim 1 in which the regulatory sequence that promotes gene expression is a viral promoter.

6. The method according to claim 1 in which the regulatory sequence that promotes gene expression is an inducible promoter.

7. The method according to claim 1 in which the selectable marker is dihydrofolate reductase.

8. The method according to claim 2 in which the selectable marker is dihydrofolate reductase and the selection is methotrexate.

9. The method according to claim 2 in which the eukaryotic cell is a mammalian cell.

10. The method according to claim 2 in which the mammalian cell is a Chinese hamster ovary cell.

11. A eukaryotic cell comprising a chromosomally integrated nucleotide sequence encoding human α-N-acetylgalactosaminidase controlled by a regulatory sequence that promotes gene expression and a selectable marker controlled by the same or different regulatory sequence, so that the α-N-acetylgalactosaminidase nucleotide sequence is stably overexpressed and an enzymatically active α-N-acetylgalactosaminidase enzyme is secreted by the eukaryotic cell.

12. The eukaryotic cell of claim 11 wherein the chromosomally integrated nucleotide sequences are amplified.

13. The eukaryotic cell according to claim 11 in which the nucleotide sequence encoding the human α-N-acetylgalactosaminidase encodes the amino acid sequence depicted in FIG. 2A to FIG. 2D from amino acid residue number 1 to 396.

14. The eukaryotic cell according to claim 11 in which the nucleotide sequence encoding the human α-N-acetylgalactosaminidase encodes the amino acid sequence depicted in FIG. 2A to FIG. 2D from amino acid residue 52 to 396.

15. The eukaryotic cell according to claim 11 in which the regulatory sequence that promotes gene expression is a viral promoter.

16. The eukaryotic cell according to claim 11 in which the regulatory sequence that promotes gene expression is an inducible promoter.

17. The eukaryotic cell according to claim 11 in which the selectable marker is dihydrofolate reductase.

18. The eukaryotic cell according to claim 12 in which the selectable marker is dihydrofolate reductase and the selection is methotrexate.

19. The eukaryotic cell according to claim 11 in which the eukaryotic cell is a mammalian cell.

20. The mammalian cell according to claim 19 in which the mammalian cell is a Chinese hamster ovary cell.

* * * * *

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
( A ) LENGTH: 2158 base pairs
( B ) TYPE: nucleic acid
( C ) STRANDEDNESS: double
( D ) TOPOLOGY: unknown ( i i ) MOLECULE TYPE: cDNA ( i x ) FEATURE:
( A ) NAME/KEY: CDS
( B ) LOCATION: 345..1580

( x i ) SEQUENCE DESCRIPTION: SEQ ID NO:1:

CTTAAGCCAG TGGCTGCCTT TTTCTGAGCC CGGGCGGGGC CGAAGGCGCC CGTAGGCCCT 60

CGGGACTCCC AGCACTGCAG AGGGTGTGAG GTCTGACATC CAAGACACGT TGTTTCGTAT 120

TTCTGAAGGA AGAACTCAAG CTCCGGGAAG TGATGGCTGG GGATGGGGCG GGCAACTTGG 180

-continued

GGACCGAGTG TACGATCCAC GCCTAAGGTT GAGGGCGGCC GAGCTAGCCA GGCAGCCGTG 240

ACCCCAGTGC TTTTCAGACG TTTCTTAGCT TCCAGAGCCC AACACATACA GCTGATACAC 300

GCAGACCAGA TCTGGTCAGG TCCTCGGAAG CTGAGTCCAG AGCG ATG CTG CTG AAG 356
Met Leu Leu Lys
1

ACA GTG CTC TTG CTG GGA CAT GTG GCC CAG GTG CTG ATG CTG GAC AAT 404
Thr Val Leu Leu Leu Gly His Val Ala Gln Val Leu Met Leu Asp Asn
5 10 15 20

GGG CTC CTG CAG ACA CCA CCC ATG GGC TGG CTG GCC TGG GAA CGC TTC 452
Gly Leu Leu Gln Thr Pro Pro Met Gly Trp Leu Ala Trp Glu Arg Phe
25 30 35

CGC TGC AAC ATT AAC TGT GAT GAG GAC CCA AAG AAC TGC ATA AGT GAA 500
Arg Cys Asn Ile Asn Cys Asp Glu Asp Pro Lys Asn Cys Ile Ser Glu
40 45 50

CAG CTC TTC ATG GAG ATG GCT GAC CGG ATG GCA CAG GAT GGA TGG CGG 548
Gln Leu Phe Met Glu Met Ala Asp Arg Met Ala Gln Asp Gly Trp Arg
55 60 65

GAC ATG GGC TAC ACA TAC CTA AAC ATT GAT GAC TGC TGG ATC GGC GGT 596
Asp Met Gly Tyr Thr Tyr Leu Asn Ile Asp Asp Cys Trp Ile Gly Gly
70 75 80

CGC GAT GCC AGT GGC CGC CTG ATG CCA GAT CCC AAG CGC TTC CCT CAT 644
Arg Asp Ala Ser Gly Arg Leu Met Pro Asp Pro Lys Arg Phe Pro His
85 90 95 100

GGC ATT CCT TTC CTG GCT GAC TAC GTT CAC TCC CTG GGC CTG AAG TTG 692
Gly Ile Pro Phe Leu Ala Asp Tyr Val His Ser Leu Gly Leu Lys Leu
105 110 115

GGT ATC TAC GCG GAC ATG GGC AAC TTC ACC TGC ATG GGT TAC CCA GGC 740
Gly Ile Tyr Ala Asp Met Gly Asn Phe Thr Cys Met Gly Tyr Pro Gly
120 125 130

ACC ACA CTG GAC AAG GTG GTC CAG GAT GCT CAG ACC TTC GCC GAG TGG 788
Thr Thr Leu Asp Lys Val Val Gln Asp Ala Gln Thr Phe Ala Glu Trp
135 140 145

AAG GTA GAC ATG CTC AAG CTG GAT GGC TGC TTC TCC ACC CCC GAG GAG 836
Lys Val Asp Met Leu Lys Leu Asp Gly Cys Phe Ser Thr Pro Glu Glu
150 155 160

CGG GCC CAG GGG TAC CCC AAG ATG GCT GCT GCC CTG AAT GCC ACA GGC 884
Arg Ala Gln Gly Tyr Pro Lys Met Ala Ala Ala Leu Asn Ala Thr Gly
165 170 175 180

CGC CCC ATC GCC TTC TCC TGC AGC TGG CCA GCC TAT GAA GGC GGC CTC 932
Arg Pro Ile Ala Phe Ser Cys Ser Trp Pro Ala Tyr Glu Gly Gly Leu
185 190 195

CCC CCA AGG GTG AAC TAC AGT CTG CTG GCG GAC ATC TGC AAC CTC TGG 980
Pro Pro Arg Val Asn Tyr Ser Leu Leu Ala Asp Ile Cys Asn Leu Trp
200 205 210

CGT AAC TAT GAT GAC ATC CAG GAC TCC TGG TGG AGC GTG CTC TCC ATC 1028
Arg Asn Tyr Asp Asp Ile Gln Asp Ser Trp Trp Ser Val Leu Ser Ile
215 220 225

CTG AAT TGG TTC GTG GAG CAC CAG GAC ATA CTG CAG CCA GTG GCC GGC 1076
Leu Asn Trp Phe Val Glu His Gln Asp Ile Leu Gln Pro Val Ala Gly
230 235 240

CCT GGG CAC TGG AAT GAC CCT GAC ATG CTG CTC ATT GGG AAC TTT GGT 1124
Pro Gly His Trp Asn Asp Pro Asp Met Leu Leu Ile Gly Asn Phe Gly
245 250 255 260

CTC AGC TTA GAG CAA TCC CGG GCC CAG ATG GCC CTG TGG ACG GTG CTG 1172
Leu Ser Leu Glu Gln Ser Arg Ala Gln Met Ala Leu Trp Thr Val Leu
265 270 275

GCA GCC CCC CTC TTG ATG TCC ACA GAC CTG CGT ACC ATC TCC GCC CAG 1220
Ala Ala Pro Leu Leu Met Ser Thr Asp Leu Arg Thr Ile Ser Ala Gln
280 285 290

AAC ATG GAC ATT CTG CAG AAT CCA CTC ATG ATC AAA ATC AAC CAG GAT 1268

-continued

```
Asn Met Asp Ile Leu Gln Asn Pro Leu Met Ile Lys Ile Asn Gln Asp
        295                 300                 305

CCC TTA GGC ATC CAG GGA CGC AGG ATT CAC AAG GAA AAA TCT CTC ATC      1316
Pro Leu Gly Ile Gln Gly Arg Arg Ile His Lys Glu Lys Ser Leu Ile
    310                 315                 320

GAA GTG TAC ATG CGG CCT CTG TCC AAC AAG GCT AGC GCC TTA GTC TTC      1364
Glu Val Tyr Met Arg Pro Leu Ser Asn Lys Ala Ser Ala Leu Val Phe
325                 330                 335                 340

TTC AGC TGC AGG ACC GAT ATG CCT TAT CGC TAC CAC TCC TCC CTT GGC      1412
Phe Ser Cys Arg Thr Asp Met Pro Tyr Arg Tyr His Ser Ser Leu Gly
                345                 350                 355

CAG CTG AAC TTC ACC GGG TCT GTG ATA TAT GAG GCC CAG GAC GTC TAC      1460
Gln Leu Asn Phe Thr Gly Ser Val Ile Tyr Glu Ala Gln Asp Val Tyr
            360                 365                 370

TCA GGT GAC ATC ATC AGT GGC CTC CGA GAT GAA ACC AAC TTC ACA GTG      1508
Ser Gly Asp Ile Ile Ser Gly Leu Arg Asp Glu Thr Asn Phe Thr Val
        375                 380                 385

ATC ATC AAC CCT TCA GGG GTA GTG ATG TGG TAC CTG TAT CCC ATC AAG      1556
Ile Ile Asn Pro Ser Gly Val Val Met Trp Tyr Leu Tyr Pro Ile Lys
    390                 395                 400

AAC CTG GAG ATG TCC CAG CAG TGAGGAGCTG GGACATGTGA CAGGCTGTGG         1607
Asn Leu Glu Met Ser Gln Gln
405                 410

TGGCACCACT GAGCCTAGAC CATGGAGCCT TGGCATGCCC AGGGCAAGTG GGGAGGTTCT    1667

CTGCTCCCCA GGCCTGCTCG GTGACTGACC CCATCATACC CAAAGTGCAA TCTCACGGCC    1727

AGGTTCTATG CCCTGTCCAA GCGTAAACCC TCTTGGAAAC TTCTTTTGGG GCAATTTTCC    1787

TGTGGCCTTC CTGGCCTCTA CTTCCATGTG CGCAGCCCCA CAGACGTTGC TGAGCAACTC    1847

GCCAGCCTCC TGAGCTCCAT GCCCATCAGG ACTCTAGCCT CTGACCTTGC TGTTGACTCT    1907

GAAATCAGGA TTTGGAAGTT TTCGAATTAG GAGTAGAGAG ATCTGACCTC TTGCCAGGAA    1967

TGCCCATGGA TCATGTGATT GGCTTTTCTA CCCATAGAGG GCCTTGCAGC CTGATACCAC    2027

TGGGAGTGAG GGTCACAAAG GAGACCTTGG CTCCCTCAGG TCACCAATAA ACCTGTTCTT    2087

TAATCAAAAA AAAAAAAAAA AAAAAAAAAA AAAAAAAAAA AAAAAAAAAA AAAAAAAAAA    2147

AAAAAAAAAA A                                                         2158
```

( 2 ) INFORMATION FOR SEQ ID NO:2:

( i ) SEQUENCE CHARACTERISTICS:
( A ) LENGTH: 411 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Leu Leu Lys Thr Val Leu Leu Leu Gly His Val Ala Gln Val Leu
 1               5                  10                  15

Met Leu Asp Asn Gly Leu Leu Gln Thr Pro Pro Met Gly Trp Leu Ala
            20                  25                  30

Trp Glu Arg Phe Arg Cys Asn Ile Asn Cys Asp Glu Asp Pro Lys Asn
        35                  40                  45

Cys Ile Ser Glu Gln Leu Phe Met Glu Met Ala Asp Arg Met Ala Gln
    50                  55                  60

Asp Gly Trp Arg Asp Met Gly Tyr Thr Tyr Leu Asn Ile Asp Asp Cys
65                  70                  75                  80

Trp Ile Gly Gly Arg Asp Ala Ser Gly Arg Leu Met Pro Asp Pro Lys
                85                  90                  95

Arg Phe Pro His Gly Ile Pro Phe Leu Ala Asp Tyr Val His Ser Leu
```

-continued 100 105 110

Gly Leu Lys Leu Gly Ile Tyr Ala Asp Met Gly Asn Phe Thr Cys Met
115 120 125

Gly Tyr Pro Gly Thr Thr Leu Asp Lys Val Val Gln Asp Ala Gln Thr
130 135 140

Phe Ala Glu Trp Lys Val Asp Met Leu Lys Leu Asp Gly Cys Phe Ser
145 150 155 160

Thr Pro Glu Glu Arg Ala Gln Gly Tyr Pro Lys Met Ala Ala Ala Leu
165 170 175

Asn Ala Thr Gly Arg Pro Ile Ala Phe Ser Cys Ser Trp Pro Ala Tyr
180 185 190

Glu Gly Gly Leu Pro Pro Arg Val Asn Tyr Ser Leu Leu Ala Asp Ile
195 200 205

Cys Asn Leu Trp Arg Asn Tyr Asp Asp Ile Gln Asp Ser Trp Trp Ser
210 215 220

Val Leu Ser Ile Leu Asn Trp Phe Val Glu His Gln Asp Ile Leu Gln
225 230 235 240

Pro Val Ala Gly Pro Gly His Trp Asn Asp Pro Asp Met Leu Leu Ile
245 250 255

Gly Asn Phe Gly Leu Ser Leu Glu Gln Ser Arg Ala Gln Met Ala Leu
260 265 270

Trp Thr Val Leu Ala Ala Pro Leu Leu Met Ser Thr Asp Leu Arg Thr
275 280 285

Ile Ser Ala Gln Asn Met Asp Ile Leu Gln Asn Pro Leu Met Ile Lys
290 295 300

Ile Asn Gln Asp Pro Leu Gly Ile Gln Gly Arg Arg Ile His Lys Glu
305 310 315 320

Lys Ser Leu Ile Glu Val Tyr Met Arg Pro Leu Ser Asn Lys Ala Ser
325 330 335

Ala Leu Val Phe Phe Ser Cys Arg Thr Asp Met Pro Tyr Arg Tyr His
340 345 350

Ser Ser Leu Gly Gln Leu Asn Phe Thr Gly Ser Val Ile Tyr Glu Ala
355 360 365

Gln Asp Val Tyr Ser Gly Asp Ile Ile Ser Gly Leu Arg Asp Glu Thr
370 375 380

Asn Phe Thr Val Ile Ile Asn Pro Ser Gly Val Val Met Trp Tyr Leu
385 390 395 400

Tyr Pro Ile Lys Asn Leu Glu Met Ser Gln Gln
405 410

( 2 ) INFORMATION FOR SEQ ID NO:3:

( i ) SEQUENCE CHARACTERISTICS:
( A ) LENGTH: 429 amino acids
( B ) TYPE: amino acid
( C ) STRANDEDNESS: single
( D ) TOPOLOGY: unknown ( i i ) MOLECULE TYPE: protein ( x i ) SEQUENCE DESCRIPTION: SEQ ID NO:3:

Met Gln Leu Arg Asn Pro Glu Leu His Leu Gly Cys Ala Leu Ala Leu
1 5 10 15

Arg Phe Leu Ala Leu Val Ser Trp Asp Ile Pro Gly Ala Arg Ala Leu
20 25 30

Asp Asn Gly Leu Ala Arg Thr Pro Thr Met Gly Trp Leu His Trp Glu
35 40 45

Arg Phe Met Cys Asn Leu Asp Cys Gln Glu Glu Pro Asp Ser Cys Ile

-continued

| | | | | | | | | | | | | | | | |
|---|---|---|---|---|---|---|---|---|---|---|---|---|---|---|---|
| | 50 | | | | | 55 | | | | | 60 | | | | |
| Ser | Glu | Lys | Leu | Phe | Met | Glu | Met | Ala | Glu | Leu | Met | Val | Ser | Glu | Gly |
| 65 | | | | | 70 | | | | | 75 | | | | | 80 |
| Trp | Lys | Asp | Ala | Gly | Tyr | Glu | Tyr | Leu | Cys | Ile | Asp | Asp | Cys | Trp | Met |
| | | | | 85 | | | | | 90 | | | | | 95 | |
| Ala | Pro | Gln | Arg | Asp | Ser | Glu | Gly | Arg | Leu | Gln | Ala | Asp | Pro | Gln | Arg |
| | | | 100 | | | | | 105 | | | | | 110 | | |
| Phe | Pro | His | Gly | Ile | Arg | Gln | Leu | Ala | Asn | Tyr | Val | His | Ser | Lys | Gly |
| | | 115 | | | | | 120 | | | | | 125 | | | |
| Leu | Lys | Leu | Gly | Ile | Tyr | Ala | Asp | Val | Gly | Asn | Lys | Thr | Cys | Ala | Gly |
| | 130 | | | | | 135 | | | | | 140 | | | | |
| Phe | Pro | Gly | Ser | Phe | Gly | Tyr | Tyr | Asp | Ile | Asp | Ala | Gln | Thr | Phe | Ala |
| 145 | | | | | 150 | | | | | 155 | | | | | 160 |
| Asp | Trp | Gly | Val | Asp | Leu | Leu | Lys | Phe | Asp | Gly | Cys | Tyr | Cys | Asp | Ser |
| | | | | 165 | | | | | 170 | | | | | 175 | |
| Leu | Glu | Asn | Leu | Ala | Asp | Gly | Tyr | Lys | His | Met | Ser | Leu | Ala | Leu | Asn |
| | | | 180 | | | | | 185 | | | | | 190 | | |
| Arg | Thr | Gly | Arg | Ser | Ile | Val | Tyr | Ser | Cys | Glu | Trp | Pro | Leu | Tyr | Met |
| | | 195 | | | | | 200 | | | | | 205 | | | |
| Trp | Pro | Phe | Gln | Lys | Pro | Asn | Tyr | Thr | Glu | Ile | Arg | Gln | Tyr | Cys | Asn |
| | 210 | | | | | 215 | | | | | 220 | | | | |
| His | Trp | Arg | Asn | Phe | Ala | Asp | Ile | Asp | Asp | Ser | Trp | Lys | Ser | Ile | Lys |
| 225 | | | | | 230 | | | | | 235 | | | | | 240 |
| Ser | Ile | Leu | Asp | Trp | Thr | Ser | Phe | Asn | Gln | Glu | Arg | Ile | Val | Asp | Val |
| | | | | 245 | | | | | 250 | | | | | 255 | |
| Ala | Gly | Pro | Gly | Gly | Trp | Asn | Asp | Pro | Asp | Met | Leu | Val | Ile | Gly | Asn |
| | | | 260 | | | | | 265 | | | | | 270 | | |
| Phe | Gly | Leu | Ser | Trp | Asn | Gln | Gln | Val | Thr | Gln | Met | Ala | Leu | Trp | Ala |
| | | 275 | | | | | 280 | | | | | 285 | | | |
| Ile | Met | Ala | Ala | Pro | Leu | Phe | Met | Ser | Asn | Asp | Leu | Arg | His | Ile | Ser |
| | 290 | | | | | 295 | | | | | 300 | | | | |
| Pro | Gln | Ala | Lys | Ala | Leu | Leu | Gln | Asp | Lys | Asp | Val | Ile | Ala | Ile | Asn |
| 305 | | | | | 310 | | | | | 315 | | | | | 320 |
| Gln | Asp | Pro | Leu | Gly | Lys | Gln | Gly | Tyr | Gln | Leu | Arg | Gln | Gly | Asp | Asn |
| | | | | 325 | | | | | 330 | | | | | 335 | |
| Phe | Glu | Val | Trp | Glu | Arg | Pro | Leu | Ser | Gly | Leu | Ala | Trp | Ala | Val | Ala |
| | | | 340 | | | | | 345 | | | | | 350 | | |
| Met | Ile | Asn | Arg | Gln | Glu | Ile | Gly | Gly | Pro | Arg | Ser | Tyr | Thr | Ile | Ala |
| | | 355 | | | | | 360 | | | | | 365 | | | |
| Val | Ala | Ser | Leu | Gly | Lys | Gly | Val | Ala | Cys | Asn | Pro | Ala | Cys | Phe | Ile |
| | 370 | | | | | 375 | | | | | 380 | | | | |
| Thr | Gln | Leu | Leu | Pro | Val | Lys | Arg | Lys | Leu | Gly | Phe | Tyr | Glu | Trp | Thr |
| 385 | | | | | 390 | | | | | 395 | | | | | 400 |
| Ser | Arg | Leu | Arg | Ser | His | Ile | Asn | Pro | Thr | Gly | Thr | Val | Leu | Leu | Gln |
| | | | | 405 | | | | | 410 | | | | | 415 | |
| Leu | Glu | Asn | Thr | Met | Gln | Met | Ser | Leu | Lys | Asp | Leu | Leu | | | |
| | | | 420 | | | | | 425 | | | | | | | |

( 2 ) INFORMATION FOR SEQ ID NO:4:

( i ) SEQUENCE CHARACTERISTICS:

( A ) LENGTH: 404 amino acids
( B ) TYPE: amino acid
( C ) STRANDEDNESS: single
( D ) TOPOLOGY: unknown ( i i ) MOLECULE TYPE: protein -continued ( x i ) SEQUENCE DESCRIPTION: SEQ ID NO:4:

Met Phe Ala Phe Tyr Phe Leu Thr Ala Cys Ile Ser Leu Lys Gly Val
1 5 10 15

Phe Gly Ser Tyr Asn Gly Leu Gly Leu Thr Pro Gln Met Gly Trp Asp
20 25 30

Asn Trp Asn Thr Phe Ala Cys Asp Val Ser Glu Gln Leu Leu Leu Asp
35 40 45

Thr Ala Asp Arg Ile Ser Asp Leu Gly Leu Lys Asp Met Gly Tyr Lys
50 55 60

Tyr Ile Ile Leu Asp Asp Cys Trp Ser Ser Gly Arg Asp Ser Asp Gly
65 70 75 80

Phe Leu Val Ala Asp Glu Gln Lys Phe Pro Asn Gly Met Gly His Val
85 90 95

Ala Asp His Leu His Asn Asn Ser Phe Leu Phe Gly Met Tyr Ser Ser
100 105 110

Ala Gly Glu Tyr Thr Cys Ala Gly Tyr Pro Gly Ser Leu Gly Arg Glu
115 120 125

Glu Glu Asp Ala Gln Phe Phe Ala Asn Asn Arg Val Asp Tyr Leu Lys
130 135 140

Tyr Asp Asn Cys Tyr Asn Lys Gly Gln Phe Gly Thr Pro Glu Ser Tyr
145 150 155 160

Arg Lys Met Ser Asp Ala Leu Asn Lys Thr Gly Arg Pro Ile Phe Tyr
165 170 175

Ser Cys Asn Trp Gly Leu Tyr Gly Ser Gly Ile Ala Asn Ser Trp Arg
180 185 190

Met Ser Gly Asp Val Thr Ala Glu Phe Thr Arg Pro Asp Ser Cys Pro
195 200 205

Asp Gly Tyr Tyr Ala Gly Phe Ser Ile Met Asn Ile Leu Asn Lys Ala
210 215 220

Ala Pro Met Gly Gln Asn Ala Gly Val Gly Gly Trp Asn Asp Leu Asp
225 230 235 240

Asn Leu Glu Val Gly Val Gly Asn Leu Thr Asp Asp Glu Glu Lys Ala
245 250 255

His Phe Ser Met Trp Ala Met Val Lys Ser Pro Leu Ile Ile Gly Ala
260 265 270

Asn Val Asn Asn Leu Lys Ala Ser Ser Tyr Ser Ile Tyr Ser Gln Ala
275 280 285

Ser Val Ile Ala Ile Asn Gln Asp Ser Asn Gly Ile Pro Ala Arg Val
290 295 300

Ser Asp Thr Asp Glu Tyr Gly Glu Ile Trp Ser Gly Pro Leu Asp Asn
305 310 315 320

Gly Asp Gln Val Val Ala Leu Leu Asn Gly Gly Ser Val Ser Arg Pro
325 330 335

Met Asn Thr Thr Leu Glu Ile Asp Ser Leu Gly Lys Lys Leu Thr Ser
340 345 350

Thr Asp Asp Leu Trp Ala Asn Arg Val Thr Ala Ser Ile Gly Arg Lys
355 360 365

Thr Gly Leu Tyr Glu Tyr Lys Asp Gly Leu Lys Asn Arg Leu Gly Gln
370 375 380

Lys Gly Ser Leu Ile Leu Asn Val Pro Ala His Ile Ala Phe Arg Leu
385 390 395 400

Arg Pro Ser Ser ( 2 ) INFORMATION FOR SEQ ID NO:5:

-continued ( i ) SEQUENCE CHARACTERISTICS:
( A ) LENGTH: 12 amino acids
( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:5:

```
Glu Gln Thr Ile Ala Asp Thr Leu Gly Pro Gly Gly
1               5                   10
```

( 2 ) INFORMATION FOR SEQ ID NO:6:

( i ) SEQUENCE CHARACTERISTICS:
( A ) LENGTH: 10 amino acids
( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:6:

```
Pro Ser Val Ile Tyr Gly Asn Val Arg Asn
1               5                   10
```

( 2 ) INFORMATION FOR SEQ ID NO:7:

( i ) SEQUENCE CHARACTERISTICS:
( A ) LENGTH: 13 amino acids
( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:7:

```
Glu Val Ala Cys Leu Val Asp Ala Asn Gly Ile Gln Pro
1               5                   10
```

( 2 ) INFORMATION FOR SEQ ID NO:8:

( i ) SEQUENCE CHARACTERISTICS:
( A ) LENGTH: 61 base pairs
( B ) TYPE: nucleic acid
( C ) STRANDEDNESS: single
( D ) TOPOLOGY: unknown ( i i ) MOLECULE TYPE: cDNA to mRNA ( x i ) SEQUENCE DESCRIPTION: SEQ ID NO:8:

```
AAUCAACAAC CAGGAUCCCU UAGGCAUCCA GGGACGCAGG AUUCACAAGG AAAAAUCUCU    60

C                                                                     61
```

( 2 ) INFORMATION FOR SEQ ID NO:9:

( i ) SEQUENCE CHARACTERISTICS:
( A ) LENGTH: 40 base pairs
( B ) TYPE: nucleic acid
( C ) STRANDEDNESS: double
( D ) TOPOLOGY: unknown ( i i ) MOLECULE TYPE: cDNA ( i v ) ANTI-SENSE: YES ( x i ) SEQUENCE DESCRIPTION: SEQ ID NO:9:

```
GTGAATCCTG CGTCCCTGGA TGCCTAAGGG ATCCTGGTTG                           40
```

( 2 ) INFORMATION FOR SEQ ID NO:10:

-continued ( i ) SEQUENCE CHARACTERISTICS:
( A ) LENGTH: 89 base pairs
( B ) TYPE: nucleic acid
( C ) STRANDEDNESS: double
( D ) TOPOLOGY: unknown ( i i ) MOLECULE TYPE: cDNA ( x i ) SEQUENCE DESCRIPTION: SEQ ID NO:10:

GGATTCACAA GGGATCCTGG ATGCCTAAGG GATCCTGCGT CCCTGGATGC CTAAGGGATC 60

CTGGGACGCA GGATTCACAA GGAAAAATC 89

( 2 ) INFORMATION FOR SEQ ID NO:11:

( i ) SEQUENCE CHARACTERISTICS:
( A ) LENGTH: 2048 base pairs
( B ) TYPE: nucleic acid
( C ) STRANDEDNESS: double
( D ) TOPOLOGY: unknown ( i i ) MOLECULE TYPE: DNA (genomic)

( x i ) SEQUENCE DESCRIPTION: SEQ ID NO:11:

CTGCTCATTG GGAACTTTGG TCTCAGCTTA GAGCAATCCC GGGCCCAGAT GGCCCTGTGG 60

ACGGTGCTGG CAGCCCCCCT CTTGATGTCC ACAGACCTGC GTACCATCTC CGCCCAGAAC 120

ATGGACATTC TGCAGAATCC ACTCATGATC AAAATCAACC AGGATCCCTT AGGCATCCAG 180

GGACGCAGGA TTCACAAGGT ACTAGGGTGT GGAGGGAAGG AAGGGGAGGG CTGAGGAACT 240

GGGTTCTCCT GAGAGAAAGG CTGCCAGCTC CCTGGGGGCA ACACCTGGCG AGGTACAGGA 300

GTCGCCCAGT CCCCAACCAG GGCTACCCCT TCTGGTTGCT TATGGTTGAG GACTCTGATG 360

GGAGCTGCTC CAACTGTCCT CCTCTTGCTG GGTGAGAGCA GGGCTGAGCA GGACAGCTCA 420

AGGGAGTCGG GGATGAGAGG TGTCAGCCAC ATAAGTGCAC ATAGCAAGGG TGAGGCACAG 480

AGCTTCTATA CACCCGTGAT GGCCTGCAGA GAGCTTGGAC TTCCCTCCAG AGCAGGAGGA 540

GCTGGTTTGT TTGTTTTTGA GACAGGGTCT CACTCTGTCA CCCAGGCTGG AGTGCAGTGG 600

CACAATTTCG ACTCACTGCA ATCTCTACCT GCCAGGTTCA AGCAATTCTC GTGCCTCAGC 660

CTCCTGAGTA GCTGGCACTA CAGGCGCCTG CACCACACCC AGCTAATTTT TGTATTTTTA 720

GTAGAGACAC CATGTTGGCC AGGCTTGTCT CGAACTCCTG GCCTCAGGTG ATCCACCCGT 780

ATCAGCCTCC CAAAGTGCTG GGATTACAGG CATGAGCACC GCACTCGGCC AGGAGAAGCT 840

GTTATAGCCA AGGAATACTA CGACTACTGG TGGCTGCTAT TTATTGAGTA CCTACCATGT 900

GCTGGGAGTT TTAGATAATT TTTCTCAGCA AGGTAGTTAT CTTGCCATTT TACAAATGAG 960

AAAAATGAAA CTTCGAGAGT CTGAGTAACT TTATCCCAAG GCTACACAGT TGGTACAAAC 1020

AAGACTGGAC TTCAGTGTCA CCTCAAAGCC TTTTTTTTTT TTTTTTTTTT TGAGATGGAG 1080

TCTCACGCTG TAGCCCAGGC TGGAGTGCAG TGGCACCATC TCAGCTCACT GCAACCTCTG 1140

GCTCCCAGGT TCAAGCGATT TTCCTGCCTC AGCCTCCCAG GTAGCTGGGA TTACAGGTGT 1200

GCGCCACCAC ACCCGGCTAA TTTTTTTTGT ATTTTTTTCA GTAGAGACAG GGTTTCACCA 1260

TGTTGGCCAG GCTACTCTCA AAACTCCTGA CGTCAGCTGA TCCACTGCCT CGGCCTCACA 1320

AAGTAATGGG ATTACAGCAT GAGCCACTGT GCCTGTCTGC CTTTGCTCTT TACCAAATCC 1380

TGGATTCTGG TAAAAAGAAA CCTACAGAAC TATGGAAGGC ACCTATAGAA CTGGTGATGC 1440

CCAGAGGAAG TAACAATTCC CTGCCAGAGG GGCTGATGGT GGAGCTGGGC CTGGAAAACC 1500

TTCTGGAGGA TGGGAGTTCA CATCCAGCTC CACTCTCCAC CCTCCTGGAA CAGAGTTCAC 1560

TGTTCCCACT GGACAGCACC CTCCAGGCCA GCACTGGCAG CTGTTTGGGG CCAGCACTCA 1620

TACGCTGTAC TGTTGTTGCG CTTCCCTGTT TCTGCGTTTA TCCCTCCCGT TGTCCTATGA 1680

-continued

GCTTCTGGGG CAGGGCTCAT GCAGCACTTG TCTCAGTGTG CTAGCATAGG GGCCGGGCTC 1740

AGAGTAGGTG TTGATGAGTA TCTGCTGAGT CAGGGAAGGT GGGCAGATAG GGTTAGATAA 1800

GCTGGGGTGC TGGAGGCCCG TGCGATCCTC CCTAAACCTG TGTGACATGG AGCTGTGAAC 1860

TGGGGGACCC AGAACTCAGG GAGGGCCAGG GAGGCAATGG TAGGTCCTGT CTGAGCAAGG 1920

GACCCCAGCC AGTAGCCACC TTCTGTGCCC AGGAAAAATC TCTCATCGAA GTGTACATGC 1980

GGCCTCTGTC CAACAAGGCT AGCGCCTTAG TCTTCTTCAG CTGCAGGACC GATATGCCTT 2040

ATCGCTAC 2048

( 2 ) INFORMATION FOR SEQ ID NO:12:

( i ) SEQUENCE CHARACTERISTICS:
( A ) LENGTH: 18 base pairs
( B ) TYPE: nucleic acid
( C ) STRANDEDNESS: single
( D ) TOPOLOGY: unknown ( i i ) MOLECULE TYPE: DNA ( x i ) SEQUENCE DESCRIPTION: SEQ ID NO:12:

CAAGACNCCN CCNATGGG 18

( 2 ) INFORMATION FOR SEQ ID NO:13:

( i ) SEQUENCE CHARACTERISTICS:
( A ) LENGTH: 34 base pairs
( B ) TYPE: nucleic acid
( C ) STRANDEDNESS: single
( D ) TOPOLOGY: unknown ( i i ) MOLECULE TYPE: DNA ( x i ) SEQUENCE DESCRIPTION: SEQ ID NO:13:

AATCATTCAG ATCGATCTGT CTGGATTCAG GNGG 34

( 2 ) INFORMATION FOR SEQ ID NO:14:

( i ) SEQUENCE CHARACTERISTICS:
( A ) LENGTH: 19 base pairs
( B ) TYPE: nucleic acid
( C ) STRANDEDNESS: single
( D ) TOPOLOGY: unknown ( i i ) MOLECULE TYPE: DNA ( x i ) SEQUENCE DESCRIPTION: SEQ ID NO:14:

ACNTTTCGCN GAAGTGGAA 19

( 2 ) INFORMATION FOR SEQ ID NO:15:

( i ) SEQUENCE CHARACTERISTICS:
( A ) LENGTH: 19 base pairs
( B ) TYPE: nucleic acid
( C ) STRANDEDNESS: single
( D ) TOPOLOGY: unknown ( i i ) MOLECULE TYPE: DNA ( x i ) SEQUENCE DESCRIPTION: SEQ ID NO:15:

TGGCCNGCNT ATCGAAGGG 19

( 2 ) INFORMATION FOR SEQ ID NO:16:

( i ) SEQUENCE CHARACTERISTICS:
( A ) LENGTH: 30 base pairs
( B ) TYPE: nucleic acid
( C ) STRANDEDNESS: single -continued ( D ) TOPOLOGY: unknown ( i i ) MOLECULE TYPE: DNA ( x i ) SEQUENCE DESCRIPTION: SEQ ID NO:16:

TCGGGACTCC CAGCACTGCA GAGGGTGTGA 30

( 2 ) INFORMATION FOR SEQ ID NO:17:

( i ) SEQUENCE CHARACTERISTICS:
( A ) LENGTH: 30 base pairs
( B ) TYPE: nucleic acid
( C ) STRANDEDNESS: single
( D ) TOPOLOGY: unknown ( i i ) MOLECULE TYPE: DNA ( x i ) SEQUENCE DESCRIPTION: SEQ ID NO:17:

CTGCAGAGGG TGTGAGGTCT GACATCCAGG 30

( 2 ) INFORMATION FOR SEQ ID NO:18:

( i ) SEQUENCE CHARACTERISTICS:
( A ) LENGTH: 30 base pairs
( B ) TYPE: nucleic acid
( C ) STRANDEDNESS: single
( D ) TOPOLOGY: unknown ( i i ) MOLECULE TYPE: DNA ( x i ) SEQUENCE DESCRIPTION: SEQ ID NO:18:

AGTCGAATTC TGATGTCCAC AGACCTGCGT 30

( 2 ) INFORMATION FOR SEQ ID NO:19:

( i ) SEQUENCE CHARACTERISTICS:
( A ) LENGTH: 30 base pairs
( B ) TYPE: nucleic acid
( C ) STRANDEDNESS: single
( D ) TOPOLOGY: unknown ( i i ) MOLECULE TYPE: DNA ( x i ) SEQUENCE DESCRIPTION: SEQ ID NO:19:

AGTCGTCGAG CATATCGGTC CTGCAGCTGA 30

( 2 ) INFORMATION FOR SEQ ID NO:20:

( i ) SEQUENCE CHARACTERISTICS:
( A ) LENGTH: 21 base pairs
( B ) TYPE: nucleic acid
( C ) STRANDEDNESS: single
( D ) TOPOLOGY: unknown ( i i ) MOLECULE TYPE: DNA ( x i ) SEQUENCE DESCRIPTION: SEQ ID NO:20:

TGGGGAGTAG ATCTGCTAAA A 21

( 2 ) INFORMATION FOR SEQ ID NO:21:

( i ) SEQUENCE CHARACTERISTICS:
( A ) LENGTH: 33 base pairs
( B ) TYPE: nucleic acid
( C ) STRANDEDNESS: single
( D ) TOPOLOGY: unknown ( i i ) MOLECULE TYPE: DNA ( x i ) SEQUENCE DESCRIPTION: SEQ ID NO:21:

GATGAGAGAT TTTTCCTGTC TAAGCTGGTA CCC 33

-continued ( 2 ) INFORMATION FOR SEQ ID NO:22:

( i ) SEQUENCE CHARACTERISTICS:
( A ) LENGTH: 33 base pairs
( B ) TYPE: nucleic acid
( C ) STRANDEDNESS: single
( D ) TOPOLOGY: unknown ( i i ) MOLECULE TYPE: DNA ( x i ) SEQUENCE DESCRIPTION: SEQ ID NO:22:

TACCAGCTTA GACAGGAAAA ATCTCTCATC GAA 33

( 2 ) INFORMATION FOR SEQ ID NO:23:

( i ) SEQUENCE CHARACTERISTICS:
( A ) LENGTH: 21 base pairs
( B ) TYPE: nucleic acid
( C ) STRANDEDNESS: single
( D ) TOPOLOGY: unknown ( i i ) MOLECULE TYPE: DNA ( x i ) SEQUENCE DESCRIPTION: SEQ ID NO:23:

AAGAGGTCAG ATCTCTCTAC T 21

( 2 ) INFORMATION FOR SEQ ID NO:24:

( i ) SEQUENCE CHARACTERISTICS:
( A ) LENGTH: 32 base pairs
( B ) TYPE: nucleic acid
( C ) STRANDEDNESS: single
( D ) TOPOLOGY: unknown ( i i ) MOLECULE TYPE: DNA ( x i ) SEQUENCE DESCRIPTION: SEQ ID NO:24:

AGTAGTAAGC TTTCATATAT CACAGACCCG GT 32